(12) United States Patent
Röse et al.

(10) Patent No.: US 11,655,297 B2
(45) Date of Patent: May 23, 2023

(54) ILDR2 ANTAGONISTS AND COMBINATIONS THEREOF

(71) Applicants: Bayer Aktiengesellschaft, Leverkusen (DE); Bayer Pharma Aktiengesellschaft, Berlin (DE); Compugen LTD., Holon (IL)

(72) Inventors: Lars Röse, Berlin (DE); Uwe Gritzan, Cologne (DE); Julia Hütter, Berlin (DE); Spencer Liang, San Mateo, CA (US); Andrew Pow, Burlington, MA (US); John Hunter, Piedmont, CA (US); Ofer Levy, Doar Na Shimson (IL); Ilan Vaknin, Modiin-Mac-cabim-Reut (IL)

(73) Assignees: Bayer Aktiengesellschaft, Leverkusen (DE); Bayer Pharma Aktiengesellschaft, Berlin (DE); Compugen LTD., Holon (IL)

( * ) Notice: Subject to any disclaimer, the term of this patent is extended or adjusted under 35 U.S.C. 154(b) by 204 days.

(21) Appl. No.: 16/766,224

(22) PCT Filed: Nov. 28, 2018

(86) PCT No.: PCT/EP2018/082779
§ 371 (c)(1),
(2) Date: May 21, 2020

(87) PCT Pub. No.: WO2019/105972
PCT Pub. Date: Jun. 6, 2019

(65) Prior Publication Data
US 2020/0369769 A1   Nov. 26, 2020

Related U.S. Application Data

(60) Provisional application No. 62/592,913, filed on Nov. 30, 2017.

(51) Int. Cl.
*C07K 16/28* (2006.01)
*A61P 35/00* (2006.01)
(Continued)

(52) U.S. Cl.
CPC ........ *C07K 16/2818* (2013.01); *A61K 31/337* (2013.01); *A61K 31/713* (2013.01); *A61P 35/00* (2018.01)

(58) Field of Classification Search
CPC ............ C07K 16/2818; C07K 16/2827; C07K 16/2803; C07K 2317/76; C07K 2317/92;
(Continued)

(56) References Cited

U.S. PATENT DOCUMENTS 5,635,483 A   6/1997 Pettit
5,780,588 A   7/1998 Pettit
(Continued)

FOREIGN PATENT DOCUMENTS

EP    0425235 A2    5/1991
WO    2009032845 A2    3/2009
(Continued)

OTHER PUBLICATIONS

Chailyan, A., et al (2011) The association of heavy and light chain variable domains in antibodies: implications for antigen specificity FEBS Journal 278; 2858-2866 (Year: 2011).*
(Continued)

*Primary Examiner* — Larry D Riggs, II
*Assistant Examiner* — Audrey L Buttice
(74) *Attorney, Agent, or Firm* — Morrison & Foerster LLP

(57) ABSTRACT

The present invention relates to a novel pharmaceutical combination comprising an ILDR2 antagonist according to any of the aforementioned claims, plus one or more other
(Continued)

therapeutically active compounds, and to novel specific ILDR2 antagonists.

18 Claims, 5 Drawing Sheets

Specification includes a Sequence Listing.

(51) Int. Cl.
*A61K 31/337* (2006.01)
*A61K 31/713* (2006.01)

(58) Field of Classification Search
CPC ............... A61K 31/337; A61K 31/713; A61K 2039/507; A61K 39/3955; A61K 2300/00; A61K 45/06; A61P 35/00; A61P 37/04
See application file for complete search history.

(56) References Cited

U.S. PATENT DOCUMENTS

| | | | |
|---|---|---|---|
| 7,498,298 B2 | 3/2009 | Doronina | |
| 9,682,123 B2 | 6/2017 | Leibel et al. | |
| 2012/0134997 A1 | 5/2012 | Levine et al. | |
| 2013/0236457 A1* | 9/2013 | Calzone | A61K 39/3955 424/143.1 |
| 2015/0158947 A1* | 6/2015 | Cojocaru | C07K 16/28 424/139.1 |
| 2017/0233473 A1 | 8/2017 | Cojocaru et al. | |

FOREIGN PATENT DOCUMENTS

| | | | |
|---|---|---|---|
| WO | 2013001517 A1 | 1/2013 | |
| WO | 2013114367 A2 | 8/2013 | |
| WO | 2015155998 A1 | 10/2015 | |
| WO | WO-2015155998 A1 * | 10/2015 | ........... A61K 31/535 |
| WO | 2017049038 A2 | 3/2017 | |
| WO | WO-2017049038 A2 * | 3/2017 | ......... C07K 16/2866 |

OTHER PUBLICATIONS

Emmons, K. M., et al (Mar. 2017) Realizing the Potential of Cancer Prevention—The Role of Implementation Science N Engl J Med 376(10); 986-990 (Year: 2017).*

Cuzick, J. (Aug. 2017) Preventive therapy for cancer Lancet Oncol 18; e472-e482 (Year: 2017).*

Chailyan, A. et al. (2011). "The association of heavy and light chain variable domains in antibodies: implications for antigen specificity," FEBS Journal 278: 2858-2866.

Chari, R.V.J. et al. (Jan. 1, 1992). "Immunoconjugates Containing Novel Maytansinoids: Promising Anticancer Drugs," Cancer Res. 52:127-131.

Cuzick, J. (Aug. 2017). "Preventive Therapy For Cancer," Lancet Oncol. 18:e472-e482.

Emmons, K. M. et al. (Mar. 9, 2017). Realizing the Potential of Cancer Prevention—The Role of Implementation Science, N. Engl. J. Med. 376(10):986-990.

Harkevich, D.A. (2010). "Famakologija. Uchebnik," Izdanie Desjatoe s. 72-82, 24 pages. English Translation.

Hecht, I. et al. (2018). "ILDR2 is a Novel B7-like Protein That Negativity Regulates T Cell Responses," J Immunol. 200(6):2025-2037.

Huetter, J. et al (2018) Discovery and preclinical characterization of BAY 1905254 a novel immune checkpoint inhibitor for cancer immunotherapy targeting the immunoglobulin-like domain containing receptor 2 (ILDR2), Cancer Research, 78(13) 1 page.

Liu, C. et al. (Aug. 1996) "Eradication of Large Colon Tumor Xenografts by Targeted Delivery of Maytansinoids," Proc. Natl. Acad. Sci. USA 93:8618-8623.

Liu, Y. et al. (2017) "Angulin proteins ILDR1 and ILDR2 regulate alternative pre-mRNA splicing through binding to splicing factors TRA2A, TRA2B, or SRSF1." Scientific Reports, 7(7466): 1-12.

Podojil, J.R. et al. (2018). "ILDR2-Fc is a Novel Regulator of Immune Homeostasis and Inducer of Antigen-Specific Immune Tolerance," J Immunol. 200(6): 2013-2024.

Söderlind E. et al. (2000), "Recombining germline-derived CDR sequences for creating diverse single-framework antibody libraries," Nature Biotech 18:852-856.

* cited by examiner

SEQUENCE LISTING

<160> NUMBER OF SEQ ID NOS: 51

<210> SEQ ID NO 1
<211> LENGTH: 5
<212> TYPE: PRT
<213> ORGANISM: artificial
<220> FEATURE:
<223> OTHER INFORMATION: 59-08.B02 BAY1905254 HCDR1

<400> SEQUENCE: 1

Ser Tyr Ala Ile Ser
1               5

<210> SEQ ID NO 2
<211> LENGTH: 17
<212> TYPE: PRT
<213> ORGANISM: artificial
<220> FEATURE:
<223> OTHER INFORMATION: 59-08.B02 BAY1905254 HCDR2

<400> SEQUENCE: 2

Gly Ile Ile Pro Ile Leu Gly Ile Ala Asn Tyr Ala Gln Lys Phe Gln
1               5                   10                  15

Gly

<210> SEQ ID NO 3
<211> LENGTH: 13
<212> TYPE: PRT
<213> ORGANISM: Artificial
<220> FEATURE:
<223> OTHER INFORMATION: 59-08.B02 BAY1905254 HCDR3

<400> SEQUENCE: 3

Ala Arg Gly Arg Leu Pro Tyr Gly Asp Phe Trp Asp Ser
1               5                   10

<210> SEQ ID NO 4
<211> LENGTH: 16
<212> TYPE: PRT
<213> ORGANISM: Artificial
<220> FEATURE:
<223> OTHER INFORMATION: 59-08.B02 BAY1905254 LCDR1

<400> SEQUENCE: 4

Arg Ser Ser Gln Ser Leu Leu Tyr Ser Asn Gly Tyr Asn Tyr Leu Asp
1               5                   10                  15

<210> SEQ ID NO 5
<211> LENGTH: 7
<212> TYPE: PRT
<213> ORGANISM: Artificial
<220> FEATURE:
<223> OTHER INFORMATION: 59-08.B02 BAY1905254 LCDR2

<400> SEQUENCE: 5

Leu Gly Ser Asn Arg Ala Ser
1               5

<210> SEQ ID NO 6
<211> LENGTH: 9
<212> TYPE: PRT
<213> ORGANISM: Artificial
<220> FEATURE:
<223> OTHER INFORMATION: 59-08.B02 BAY1905254 LCDR3

<400> SEQUENCE: 6

Met Gln Ala Leu Gln Thr Pro Leu Thr
1               5

<210> SEQ ID NO 7
<211> LENGTH: 120
<212> TYPE: PRT
<213> ORGANISM: Artificial
<220> FEATURE:

<223> OTHER INFORMATION: 59-08.B02 heavy chain VD| BAY1905254

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Leu Pro Tyr Gly Asp Phe Trp Asp Ser Trp Gly Gln
            100                 105                 110

Gly Thr Leu Val Thr Val Ser Ser
        115                 120

<210> SEQ ID NO 8
<211> LENGTH: 112
<212> TYPE: PRT
<213> ORGANISM: Artificial
<220> FEATURE:
<223> OTHER INFORMATION: 59-08.B02-light chain VD| BAY1905254

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Leu Glu Ile Arg
            100                 105                 110

<210> SEQ ID NO 9
<211> LENGTH: 121
<212> TYPE: PRT
<213> ORGANISM: Artificial
<220> FEATURE:
<223> OTHER INFORMATION: 61-02.C05 heavy chain VD

<400> SEQUENCE: 9

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ser Gly Ser Thr Gln Tyr Ala Asp Ser Val
        50                  55                  60

Lys Gly Arg Phe Thr Val Ser Arg Asp Asn Ser Lys Asn Thr Leu Tyr
65                  70                  75                  80

Leu Gln Met Lys Ser Leu Arg Ala Glu Asp Thr Ala Leu Tyr Tyr Cys
                85                  90                  95

Ala Lys Asp Phe Val Gly Val Leu Pro Asp Ala Phe Asp Ile Trp Gly
                100                 105                 110

Gln Gly Thr Met Val Thr Val Ser Ser
            115                 120

<210> SEQ ID NO 10
<211> LENGTH: 107
<212> TYPE: PRT
<213> ORGANISM: Artificial
<220> FEATURE:
<223> OTHER INFORMATION: 61-02.C05 light chain VD

<400> SEQUENCE: 10

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Thr Asn Lys Tyr
                20                  25                  30

Leu Asn Trp Tyr Gln Gln Lys Pro Gly Lys Ala Pro Glu Leu Leu Ile
            35                  40                  45

Tyr Gly Ala Ser Thr Leu Glu Ser Gly Val Pro Pro Arg Phe Ser Ala
        50                  55                  60

Ser Gly Ser Gly Thr Asp Phe Thr Leu Thr Ile Asn Ser Leu Gln Pro
65                  70                  75                  80

Glu Asp Ile Gly Arg Tyr Tyr Cys Gln Gln Tyr His Ile Pro Pro Pro
                85                  90                  95

Ser Phe Gly Gly Gly Thr Lys Leu Glu Ile Lys
            100                 105

<210> SEQ ID NO 11
<211> LENGTH: 115
<212> TYPE: PRT
<213> ORGANISM: Artificial
<220> FEATURE:
<223> OTHER INFORMATION: 56-02.E08 heavy chain VD

<400> SEQUENCE: 11

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Ser Phe Thr Thr Tyr
                20                  25                  30

Trp Ile Gly Trp Val Arg Gln Val Pro Gly Lys Gly Leu Glu Trp Met
            35                  40                  45

Gly Ile Ile Tyr Pro Gly Asp Tyr Asp Thr Arg Tyr Ser Pro Ser Phe
        50                  55                  60

Gln Gly Gln Val Thr Ile Ser Ala Asp Lys Ser Ile Asn Thr Ala Tyr
65                  70                  75                  80

Leu Gln Trp Ser Ser Leu Glu Ala Ser Asp Ser Ala Met Tyr Tyr Cys
                85                  90                  95

Ala Ile Gly Glu Pro Phe Asp Tyr Trp Gly Gln Gly Thr Leu Val Thr
                100                 105                 110

Val Ser Ser
    115

<210> SEQ ID NO 12
<211> LENGTH: 112
<212> TYPE: PRT
<213> ORGANISM: Artificial
<220> FEATURE:
<223> OTHER INFORMATION: 56-02.E08 light chain VD

<400> SEQUENCE: 12

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ala
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 13
<211> LENGTH: 131
<212> TYPE: PRT
<213> ORGANISM: artificial
<220> FEATURE:
<223> OTHER INFORMATION: 74.15.G09 heavy chain VD

<400> SEQUENCE: 13

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Ser Pro Ser Val Gly Leu Gly Ser Tyr Tyr Asp Phe Trp
            100                 105                 110

Ser Gly Leu Tyr Gly Met Asp Val Trp Gly Gln Gly Thr Thr Val Thr
        115                 120                 125

Val Ser Ser
    130

<210> SEQ ID NO 14
<211> LENGTH: 108
<212> TYPE: PRT

<213> ORGANISM: Artificial
<220> FEATURE:
<223> OTHER INFORMATION: 74.15.G09 light chain VD

<400> SEQUENCE: 14

Glu Ile Val Leu Thr Gln Ser Pro Gly Thr Leu Ser Leu Ser Pro Gly
1               5                   10                  15

Glu Arg Val Thr Leu Ser Cys Arg Thr Gly Gln Arg Val Glu Asn Leu
            20                  25                  30

Phe Ile Ala Trp Tyr Gln Gln Lys Pro Gly Gln Ala Pro Arg Leu Leu
        35                  40                  45

Leu Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Tyr Asp Asp Ser Gly
                85                  90                  95

Ile Thr Phe Gly Gln Gly Thr Arg Leu Glu Ile Lys
            100                 105

<210> SEQ ID NO 15
<211> LENGTH: 125
<212> TYPE: PRT
<213> ORGANISM: Artificial
<220> FEATURE:
<223> OTHER INFORMATION: 56.02.E10 heavy chain VD

<400> SEQUENCE: 15

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Pro Glu Trp Leu
        35                  40                  45

Ala Phe Ile Arg Tyr Asp Gly Ser Lys Lys Tyr Tyr Ala Asp Ser Val
    50                  55                  60

Arg Gly Arg Phe Thr Ile Ser Arg Asp Asn Ser Lys Asn Met Leu Tyr
65                  70                  75                  80

Leu Gln Met Asn Ser Leu Arg Thr Glu Asp Thr Ala Val Tyr Tyr Cys
                85                  90                  95

Ala Lys Glu Gly Ile Ala Ala Pro Gly Ser Gly Tyr Tyr Tyr Gly Met
            100                 105                 110

Asp Val Trp Gly Gln Gly Thr Thr Val Thr Val Ser Ser
        115                 120                 125

<210> SEQ ID NO 16
<211> LENGTH: 109
<212> TYPE: PRT
<213> ORGANISM: Artificial
<220> FEATURE:
<223> OTHER INFORMATION: 56.02.E10 light chain VD

<400> SEQUENCE: 16

Gln Ser Ala Leu Thr Gln Pro Ala Ser Val Ser Gly Ser Pro Gly Gln
1               5                   10                  15

Ser Ile Thr Ile Ser Cys Ser Gly Thr Thr Asp Val Gly Arg Tyr
            20                  25                  30

Thr Leu Val Ser Trp Tyr Gln His Pro Gly Lys Ala Pro Lys Leu
        35                  40                  45

Ile Ile Phe Glu Val Asn Lys Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Phe Cys Cys Ser Tyr Thr Gly Thr
                85                  90                  95

Thr Val Ile Phe Gly Gly Gly Thr Gln Leu Thr Val Leu
            100                 105

<210> SEQ ID NO 17
<211> LENGTH: 20
<212> TYPE: DNA
<213> ORGANISM: Artificial
<220> FEATURE:
<223> OTHER INFORMATION: CPG Oligo nucleotide ODN 1826

<400> SEQUENCE: 17
tccatgacgt tcctgacgtt                                              20

<210> SEQ ID NO 18
<211> LENGTH: 5
<212> TYPE: PRT
<213> ORGANISM: Artificial
<220> FEATURE:
<223> OTHER INFORMATION: 61-02.C05 HCDR1

<400> SEQUENCE: 18

Ser Tyr Ala Met Ser
1               5

<210> SEQ ID NO 19
<211> LENGTH: 17
<212> TYPE: PRT
<213> ORGANISM: Artificial
<220> FEATURE:
<223> OTHER INFORMATION: 61-02.C05 HCDR2

<400> SEQUENCE: 19

Gly Ile Ser Ser Ser Gly Gly Ser Thr Gln Tyr Ala Asp Ser Val Lys
1               5                   10                  15

Gly

<210> SEQ ID NO 20
<211> LENGTH: 12
<212> TYPE: PRT
<213> ORGANISM: Artificial
<220> FEATURE:
<223> OTHER INFORMATION: 61-02.C05 HCDR3

<400> SEQUENCE: 20

Asp Phe Val Gly Val Leu Pro Asp Ala Phe Asp Ile
1               5                   10

<210> SEQ ID NO 21
<211> LENGTH: 11
<212> TYPE: PRT
<213> ORGANISM: artificial
<220> FEATURE:
<223> OTHER INFORMATION: 61-02.C05 LCDR1

<400> SEQUENCE: 21

Gln Ala Ser Gln Asp Thr Asn Lys Tyr Leu Asn
1               5                   10

```
<210> SEQ ID NO 22
<211> LENGTH: 7
<212> TYPE: PRT
<213> ORGANISM: Artificial
<220> FEATURE:
<223> OTHER INFORMATION: 61-02.C05 LCDR2

<400> SEQUENCE: 22

Gly Ala Ser Thr Leu Glu Ser
1               5

<210> SEQ ID NO 23
<211> LENGTH: 9
<212> TYPE: PRT
<213> ORGANISM: Artificial
<220> FEATURE:
<223> OTHER INFORMATION: 61-02.C05 LCDR3

<400> SEQUENCE: 23

Gln Gln Tyr His Ile Pro Pro Pro Ser
1               5

<210> SEQ ID NO 24
<211> LENGTH: 5
<212> TYPE: PRT
<213> ORGANISM: Artificial
<220> FEATURE:
<223> OTHER INFORMATION: 56-02.E08 HCDR1

<400> SEQUENCE: 24

Thr Tyr Trp Ile Gly
1               5

<210> SEQ ID NO 25
<211> LENGTH: 17
<212> TYPE: PRT
<213> ORGANISM: Artificial
<220> FEATURE:
<223> OTHER INFORMATION: 56-02.E08 HCDR2

<400> SEQUENCE: 25

Ile Ile Tyr Pro Gly Asp Tyr Asp Thr Arg Tyr Ser Pro Ser Phe Gln
1               5                   10                  15

Gly

<210> SEQ ID NO 26
<211> LENGTH: 8
<212> TYPE: PRT
<213> ORGANISM: Artificial
<220> FEATURE:
<223> OTHER INFORMATION: 56-02.E08 HCDR3

<400> SEQUENCE: 26

Ala Ile Gly Glu Pro Phe Asp Tyr
1               5

<210> SEQ ID NO 27
<211> LENGTH: 16
<212> TYPE: PRT
<213> ORGANISM: Artificial
<220> FEATURE:
<223> OTHER INFORMATION: 56-02.E08 LCDR1

<400> SEQUENCE: 27

Arg Ser Ser Gln Ser Leu Leu His Ala Asn Gly Tyr Asn Tyr Leu Asp
1               5                   10                  15
```

```
<210> SEQ ID NO 28
<211> LENGTH: 7
<212> TYPE: PRT
<213> ORGANISM: Artificial
<220> FEATURE:
<223> OTHER INFORMATION: 56-02.E08 LCDR2

<400> SEQUENCE: 28

Leu Gly Ser Asn Arg Ala Ser
1               5

<210> SEQ ID NO 29
<211> LENGTH: 9
<212> TYPE: PRT
<213> ORGANISM: Artificial
<220> FEATURE:
<223> OTHER INFORMATION: 56-02.E08 LCDR3

<400> SEQUENCE: 29

Met Gln Ala Leu Gln Thr Pro Leu Thr
1               5

<210> SEQ ID NO 30
<211> LENGTH: 5
<212> TYPE: PRT
<213> ORGANISM: Artificial
<220> FEATURE:
<223> OTHER INFORMATION: 74.15.G09 HCDR1

<400> SEQUENCE: 30

Ser Tyr Gly Met His
1               5

<210> SEQ ID NO 31
<211> LENGTH: 17
<212> TYPE: PRT
<213> ORGANISM: Artificial
<220> FEATURE:
<223> OTHER INFORMATION: 74.15.G09 HCDR2

<400> SEQUENCE: 31

Val Ile Ser Tyr Asp Gly Ser Asn Lys Tyr Tyr Ala Asp Ser Val Lys
1               5                   10                  15

Gly

<210> SEQ ID NO 32
<211> LENGTH: 24
<212> TYPE: PRT
<213> ORGANISM: Artificial
<220> FEATURE:
<223> OTHER INFORMATION: 74.15.G09 HCDR3

<400> SEQUENCE: 32

Ala Lys Glu Ser Pro Ser Val Gly Leu Gly Ser Tyr Tyr Asp Phe Trp
1               5                   10                  15

Ser Gly Leu Tyr Gly Met Asp Val
            20

<210> SEQ ID NO 33
<211> LENGTH: 12
<212> TYPE: PRT
<213> ORGANISM: Artificial
<220> FEATURE:
<223> OTHER INFORMATION: 74.15.G09 LCDR1
```

```
<400> SEQUENCE: 33

Arg Thr Gly Gln Arg Val Glu Asn Leu Phe Ile Ala
1               5                   10

<210> SEQ ID NO 34
<211> LENGTH: 7
<212> TYPE: PRT
<213> ORGANISM: Artificial
<220> FEATURE:
<223> OTHER INFORMATION: 74.15.G09 LCDR2

<400> SEQUENCE: 34

Gly Ala Ser Asn Arg Ala Thr
1               5

<210> SEQ ID NO 35
<211> LENGTH: 9
<212> TYPE: PRT
<213> ORGANISM: Artificial
<220> FEATURE:
<223> OTHER INFORMATION: 74.15.G09 LCDR3

<400> SEQUENCE: 35

Gln Gln Tyr Asp Asp Ser Gly Ile Thr
1               5

<210> SEQ ID NO 36
<211> LENGTH: 5
<212> TYPE: PRT
<213> ORGANISM: Artificial
<220> FEATURE:
<223> OTHER INFORMATION: 56.02.E10 HCDR1

<400> SEQUENCE: 36

Asn Tyr Gly Met His
1               5

<210> SEQ ID NO 37
<211> LENGTH: 17
<212> TYPE: PRT
<213> ORGANISM: Artificial
<220> FEATURE:
<223> OTHER INFORMATION: 56.02.E10 HCDR2

<400> SEQUENCE: 37

Phe Ile Arg Tyr Asp Gly Ser Lys Lys Tyr Tyr Ala Asp Ser Val Arg
1               5                   10                  15

Gly

<210> SEQ ID NO 38
<211> LENGTH: 16
<212> TYPE: PRT
<213> ORGANISM: Artificial
<220> FEATURE:
<223> OTHER INFORMATION: 56.02.E10 HCDR3

<400> SEQUENCE: 38

Glu Gly Ile Ala Ala Pro Gly Ser Gly Tyr Tyr Tyr Gly Met Asp Val
1               5                   10                  15

<210> SEQ ID NO 39
<211> LENGTH: 14
<212> TYPE: PRT
<213> ORGANISM: Artificial
<220> FEATURE:
<223> OTHER INFORMATION: 56.02.E10 LCDR1
```

<400> SEQUENCE: 39

Ser Gly Thr Thr Thr Asp Val Gly Arg Tyr Thr Leu Val Ser
1               5                   10

<210> SEQ ID NO 40
<211> LENGTH: 7
<212> TYPE: PRT
<213> ORGANISM: Artificial
<220> FEATURE:
<223> OTHER INFORMATION: 56.02.E10 LCDR2

<400> SEQUENCE: 40

Glu Val Asn Lys Arg Pro Ser
1               5

<210> SEQ ID NO 41
<211> LENGTH: 9
<212> TYPE: PRT
<213> ORGANISM: Artificial
<220> FEATURE:
<223> OTHER INFORMATION: 56.02.E10 LCDR3

<400> SEQUENCE: 41

Cys Ser Tyr Thr Gly Thr Thr Val Ile
1               5

<210> SEQ ID NO 42
<211> LENGTH: 445
<212> TYPE: PRT
<213> ORGANISM: Artificial
<220> FEATURE:
<223> OTHER INFORMATION: 59-08.B02 heavy chain BAY1905254

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Leu Pro Tyr Gly Asp Phe Trp Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

```
Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
210                 215                 220

Glu Cys Pro Pro Cys Pro Ala Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Phe Arg Val Val Ser Val
        290                 295                 300

Leu Thr Val Val His Gln Asp Trp Leu Asn Gly Lys Glu Tyr Lys Cys
305                 310                 315                 320

Lys Val Ser Asn Lys Gly Leu Pro Ala Pro Ile Glu Lys Thr Ile Ser
                325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 43
<211> LENGTH: 219
<212> TYPE: PRT
<213> ORGANISM: Artificial
<220> FEATURE:
<223> OTHER INFORMATION: 59-08.B02-light chain BAY1905254

<400> SEQUENCE: 43

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Leu Glu Ile Arg
            100                 105                 110
```

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 44
<211> LENGTH: 446
<212> TYPE: PRT
<213> ORGANISM: Artificial
<220> FEATURE:
<223> OTHER INFORMATION: 61-02.C05 heavy chain

<400> SEQUENCE: 44

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ser Gly Gly Ser Thr Gln Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Lys Ser Leu Arg Ala Glu Asp Thr Ala Leu Tyr Tyr Cys
            85                  90                  95

Ala Lys Asp Phe Val Gly Val Leu Pro Asp Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
            245                 250                 255

```
Pro Glu Val Thr Cys Val Val Asp Val Ser His Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 45
<211> LENGTH: 214
<212> TYPE: PRT
<213> ORGANISM: Artificial
<220> FEATURE:
<223> OTHER INFORMATION: 61-02.C05 light chain

<400> SEQUENCE: 45

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Thr Asn Lys Tyr
            20                  25                  30

Leu Asn Trp Tyr Gln Gln Lys Pro Gly Lys Ala Pro Glu Leu Leu Ile
        35                  40                  45

Tyr Gly Ala Ser Thr Leu Glu Ser Gly Val Pro Pro Arg Phe Ser Ala
    50                  55                  60

Ser Gly Ser Gly Thr Asp Phe Thr Leu Thr Ile Asn Ser Leu Gln Pro
65                  70                  75                  80

Glu Asp Ile Gly Arg Tyr Tyr Cys Gln Gln Tyr His Ile Pro Pro Pro
                85                  90                  95

Ser Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 46
<211> LENGTH: 440
<212> TYPE: PRT
<213> ORGANISM: Artificial
<220> FEATURE:
<223> OTHER INFORMATION: 56-02.E08 heavy chain

<400> SEQUENCE: 46

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Ser Phe Thr Thr Tyr
            20                  25                  30

Trp Ile Gly Trp Val Arg Gln Val Pro Gly Lys Gly Leu Glu Trp Met
        35                  40                  45

Gly Ile Ile Tyr Pro Gly Asp Tyr Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Glu Ala Ser Asp Ser Ala Met Tyr Tyr Cys
                85                  90                  95

Ala Ile Gly Glu Pro Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Asn Phe Gly
            180                 185                 190

Thr Gln Thr Tyr Thr Cys Asn Val Asp His Lys Pro Ser Asn Thr Lys
        195                 200                 205

Val Asp Lys Thr Val Glu Arg Lys Cys Cys Val Glu Cys Pro Pro Cys
    210                 215                 220

Pro Ala Pro Pro Val Ala Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Gln Phe Asn Trp Tyr
            260                 265                 270

Val Asp Gly Val Glu Val His Asn Ala Lys Thr Lys Pro Arg Glu Glu
        275                 280                 285

Gln Phe Asn Ser Thr Phe Arg Val Val Ser Val Leu Thr Val Val His
    290                 295                 300

Gln Asp Trp Leu Asn Gly Lys Glu Tyr Lys Cys Lys Val Ser Asn Lys
305                 310                 315                 320
```

```
Gly Leu Pro Ala Pro Ile Glu Lys Thr Ile Ser Lys Thr Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Met Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly
        435                 440

<210> SEQ ID NO 47
<211> LENGTH: 219
<212> TYPE: PRT
<213> ORGANISM: Artificial
<220> FEATURE:
<223> OTHER INFORMATION: 56-02.E08 light chain

<400> SEQUENCE: 47

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ala
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 48
```

```
<211> LENGTH: 456
<212> TYPE: PRT
<213> ORGANISM: Artificial
<220> FEATURE:
<223> OTHER INFORMATION: 74.15.G09 heavy chain

<400> SEQUENCE: 48
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Val | Val | Gln | Pro | Gly | Arg | |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Tyr |
| | | | 20 | | | | | 25 | | | | | 30 | | |
| Gly | Met | His | Trp | Val | Arg | Gln | Ala | Pro | Gly | Lys | Gly | Leu | Glu | Trp | Val |
| | | | 35 | | | | | 40 | | | | | 45 | | |
| Ala | Val | Ile | Ser | Tyr | Asp | Gly | Ser | Asn | Lys | Tyr | Tyr | Ala | Asp | Ser | Val |
| | | | 50 | | | | | 55 | | | | | 60 | | |
| Lys | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Tyr | Cys |
| | | | | 85 | | | | | 90 | | | | | 95 | |
| Ala | Lys | Glu | Ser | Pro | Ser | Val | Gly | Leu | Gly | Ser | Tyr | Tyr | Asp | Phe | Trp |
| | | | | 100 | | | | | 105 | | | | | 110 | |
| Ser | Gly | Leu | Tyr | Gly | Met | Asp | Val | Trp | Gly | Gln | Gly | Thr | Thr | Val | Thr |
| | | | | 115 | | | | | 120 | | | | | 125 | |
| Val | Ser | Ser | Ala | Ser | Thr | Lys | Gly | Pro | Ser | Val | Phe | Pro | Leu | Ala | Pro |
| 130 | | | | | 135 | | | | | 140 | | | | | |
| Cys | Ser | Arg | Ser | Thr | Ser | Glu | Ser | Thr | Ala | Ala | Leu | Gly | Cys | Leu | Val |
| 145 | | | | | 150 | | | | | 155 | | | | | 160 |
| Lys | Asp | Tyr | Phe | Pro | Glu | Pro | Val | Thr | Val | Ser | Trp | Asn | Ser | Gly | Ala |
| | | | | 165 | | | | | 170 | | | | | 175 | |
| Leu | Thr | Ser | Gly | Val | His | Thr | Phe | Pro | Ala | Val | Leu | Gln | Ser | Ser | Gly |
| | | | | 180 | | | | | 185 | | | | | 190 | |
| Leu | Tyr | Ser | Leu | Ser | Ser | Val | Val | Thr | Val | Pro | Ser | Ser | Asn | Phe | Gly |
| | | | | 195 | | | | | 200 | | | | | 205 | |
| Thr | Gln | Thr | Tyr | Thr | Cys | Asn | Val | Asp | His | Lys | Pro | Ser | Asn | Thr | Lys |
| | | | | 210 | | | | | 215 | | | | | 220 | |
| Val | Asp | Lys | Thr | Val | Glu | Arg | Lys | Cys | Cys | Val | Glu | Cys | Pro | Pro | Cys |
| 225 | | | | | 230 | | | | | 235 | | | | | 240 |
| Pro | Ala | Pro | Pro | Val | Ala | Gly | Pro | Ser | Val | Phe | Leu | Phe | Pro | Pro | Lys |
| | | | | 245 | | | | | 250 | | | | | 255 | |
| Pro | Lys | Asp | Thr | Leu | Met | Ile | Ser | Arg | Thr | Pro | Glu | Val | Thr | Cys | Val |
| | | | | 260 | | | | | 265 | | | | | 270 | |
| Val | Val | Asp | Val | Ser | His | Glu | Asp | Pro | Glu | Val | Gln | Phe | Asn | Trp | Tyr |
| | | | | 275 | | | | | 280 | | | | | 285 | |
| Val | Asp | Gly | Val | Glu | Val | His | Asn | Ala | Lys | Thr | Lys | Pro | Arg | Glu | Glu |
| | | | | 290 | | | | | 295 | | | | | 300 | |
| Gln | Phe | Asn | Ser | Thr | Phe | Arg | Val | Val | Ser | Val | Leu | Thr | Val | Val | His |
| 305 | | | | | 310 | | | | | 315 | | | | | 320 |
| Gln | Asp | Trp | Leu | Asn | Gly | Lys | Glu | Tyr | Lys | Cys | Lys | Val | Ser | Asn | Lys |
| | | | | 325 | | | | | 330 | | | | | 335 | |
| Gly | Leu | Pro | Ala | Pro | Ile | Glu | Lys | Thr | Ile | Ser | Lys | Thr | Lys | Gly | Gln |
| | | | | 340 | | | | | 345 | | | | | 350 | |
| Pro | Arg | Glu | Pro | Gln | Val | Tyr | Thr | Leu | Pro | Pro | Ser | Arg | Glu | Glu | Met |
| | | | | 355 | | | | | 360 | | | | | 365 | |
| Thr | Lys | Asn | Gln | Val | Ser | Leu | Thr | Cys | Leu | Val | Lys | Gly | Phe | Tyr | Pro |
| | | | | 370 | | | | | 375 | | | | | 380 | |

```
Ser Asp Ile Ala Val Glu Trp Glu Ser Asn Gly Gln Pro Glu Asn Asn
385                 390                 395                 400

Tyr Lys Thr Thr Pro Pro Met Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly
    450                 455

<210> SEQ ID NO 49
<211> LENGTH: 215
<212> TYPE: PRT
<213> ORGANISM: Artificial
<220> FEATURE:
<223> OTHER INFORMATION: 74.15.G09 light chain

<400> SEQUENCE: 49

Glu Ile Val Leu Thr Gln Ser Pro Gly Thr Leu Ser Leu Ser Pro Gly
1               5                   10                  15

Glu Arg Val Thr Leu Ser Cys Arg Thr Gly Gln Arg Val Glu Asn Leu
            20                  25                  30

Phe Ile Ala Trp Tyr Gln Gln Lys Pro Gly Gln Ala Pro Arg Leu Leu
        35                  40                  45

Leu Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Tyr Asp Asp Ser Gly
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 50
<211> LENGTH: 450
<212> TYPE: PRT
<213> ORGANISM: Artificial
<220> FEATURE:
<223> OTHER INFORMATION: 56.02.E10 heavy chain
```

<400> SEQUENCE: 50

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Pro Glu Trp Leu
        35                  40                  45

Ala Phe Ile Arg Tyr Asp Gly Ser Lys Lys Tyr Ala Asp Ser Val
    50                  55                  60

Arg Gly Arg Phe Thr Ile Ser Arg Asp Asn Ser Lys Asn Met Leu Tyr
65                  70                  75                  80

Leu Gln Met Asn Ser Leu Arg Thr Glu Asp Thr Ala Val Tyr Tyr Cys
                85                  90                  95

Ala Lys Glu Gly Ile Ala Ala Pro Gly Ser Gly Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Met Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 51
<211> LENGTH: 215
<212> TYPE: PRT
<213> ORGANISM: Artificial
<220> FEATURE:
<223> OTHER INFORMATION: 56.02.E10 light chain

<400> SEQUENCE: 51

Gln Ser Ala Leu Thr Gln Pro Ala Ser Val Ser Gly Ser Pro Gly Gln
1               5                   10                  15

Ser Ile Thr Ile Ser Cys Ser Gly Thr Thr Asp Val Gly Arg Tyr
            20                  25                  30

Thr Leu Val Ser Trp Tyr Gln His Pro Gly Lys Ala Pro Lys Leu
        35                  40                  45

Ile Ile Phe Glu Val Asn Lys Arg Pro Ser Gly Val Ser Ser Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Phe Cys Cys Ser Tyr Thr Gly Thr
                85                  90                  95

Thr Val Ile Phe Gly Gly Gly Thr Gln Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
210                 215
```

ILDR2 ANTAGONISTS AND COMBINATIONS THEREOF

CROSS REFERENCE TO RELATED APPLICATIONS

This application is a national stage application under 35 U.S.C. § 371 of International Application No. PCT/EP2018/082779, filed internationally on Nov. 28, 2018, which claims the benefit of U.S. Provisional Application No. 62/592,913, filed Nov. 30, 2017.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052041700SEQLIST.TXT, date recorded: May 2, 2020, size: 46 KB).

FIELD OF THE INVENTION

The present invention relates to a novel pharmaceutical combination comprising an ILDR2 antagonist, plus one or more other therapeutically active compounds, as well as novel specific ILDR2 antagonists.

BACKGROUND

The B7 family of immune-regulatory ligands consists of structurally related, cell-surface protein ligands, which bind to receptors on lymphocytes that regulate immune responses.

The activation of T and B lymphocytes is initiated by engagement of cell-surface, antigen-specific T cell receptors or B cell receptors, but additional signals delivered simultaneously by B7 ligands determine the ultimate immune response. These 'costimulatory' or 'coinhibitory' signals are delivered by B7 ligands through the CD28 family of receptors on lymphocytes.

The family of B7 proteins includes: B7.1 (CD80), B7.2 (CD86), inducible costimulator ligand (ICOS-L), programmed death-1 ligand (PD-L1, also called B7-1)), programmed death-2 ligand (PD-L2), B7-H3, and B7-H4. Members of the family have been characterized predominantly in humans and mice, but some members are also found in birds. They share 20-40% amino-acid identity and are structurally related, with the extracellular domain containing tandem domains related to variable and constant immunoglobulin domains. B7 ligands are expressed in lymphoid and non-lymphoid tissues. The importance of the family in regulating immune responses is shown by the development of immunodeficiency and autoimmune diseases in mice with mutations in B7-family genes. Manipulation of the signals delivered by B7 ligands has shown potential in the treatment of autoimmunity, inflammatory diseases and cancer.

The interaction of B7-family members with their respective costimulatory receptor, usually a member of the CD28-related family, augments immune responses, while interaction with co-inhibitory receptors, such as CTLA4, attenuates immune responses.

Clearly, each B7 molecule has developed its own niche in the immune system. As specific niches of B7 family members continue to be dissected, their diagnostic and therapeutic potential becomes ever more apparent. Many of the B7 superfamily members were initially characterized as T cell co-stimulatory molecules. However, more recently it has become clear they can also co-inhibit T cell responses. Thus, B7 family members may have opposing effects on an immune response.

Members of the B7 family have become targets for immune checkpoint inhibitor therapy.

The PD-L1 inhibitor atezolizumab (MPDL3280) is a fully humanized, engineered, IgG1 antibody which has efficacy in the treatment of a number of different cancers, including melanoma, lung, bladder and renal cancer. Avelumab (MSB0010718C) is a fully human IgG1 antibody which has shown efficacy in metastatic or locally advanced solid tumors. Durvalumab is an anti-PD-L1 antibody that has shown efficacy in metastatic urothelial bladder cancer in combination with an alternative immune checkpoint inhibitor.

The PD1 inhibitors nivolumab and pembrolizumab bind to the PD-L1 receptor PD-1 and inhibit binding of PD-L1 to PD-1.

Tremelimumab (formerly ticilimumab, CP-675,206) is a fully human monoclonal antibody (IgG2) against CTLA-4. It blocks the binding of the antigen-presenting cell ligands B7.1 and B7.2 to CTLA-4, resulting in inhibition of B7-CTLA-4-mediated downregulation of T cell activation. Ipilimumab is a similar antibody with a similar mode of action, yet of the IgG1 isotype.

Enoblituzumab (also referred to as MGA271) is an antibody that target B7-H3, which is over-expressed on tumor cells and cancer stem-like cells, as well as on the supporting tumor vasculature and underlying tissues, or stroma.

However, despite the great success of the above identified approaches, it has turned out that some of them are either not sustainable in their efficacy, i.e., a recurrence of the disease, occurs, and/or are not efficacious with regard to a given disease type.

Therefore there is a great need in the field of immune checkpoint inhibitor therapy for providing new and improved therapies as well as for improving existing therapies.

The recently identified ILDR2 (Immunoglobulin Like Domain Containing Receptor 2), also known as C1ORF32, is a novel member of the B7/CD28 family. ILDR2 comprises an IgV domain; in addition of it being a type I membrane protein, like other known B7 members—which eventually gave rise to its annotation to the B7 family. Also, two alternatively spliced variants of ILDR2 (H19011-1-P8 and H19011-1-P9), which share only the first 5 exons with the wild type C1ORF32 are similar to the known B7 family members in their exons' sizes and the position of the IgV and transmembrane domains within these exons. For a thorough characterization of ILDR2, see WO2009032845, the content of which is incorporated by reference herein.

Thus far, no therapies targeting this recently identified receptor have been developed. It is hence one object of the present invention to provide new and improved immune checkpoint inhibitor therapies targeting ILDR2.

SUMMARY OF THE INVENTION

The present invention provides a novel pharmaceutical combination comprising an ILDR2 antagonist, plus one or more other therapeutically active compounds, as well as novel specific ILDR2 antagonists. The invention and general advantages of its features will be discussed in detail below.

BRIEF DESCRIPTION OF THE FIGURES

The term "mIgG" refers to a murine immunoglobulin G. The term "hIgG" refers to a human immunoglobulin G.

The terms "aPD-L1", "aPDL1", "aILDR2" and "BAY1905254" are defined elsewhere herein.

The term "isotype control" refers to the use of a monoclonal antibody of the same isotype, same species, but directed against an irrelevant antigen. Isotype controls are widely used to set the discriminatory level between non-specific background and positive fluorescent staining.

The term "isotype ADC" refers to the use of an Antibody Drug Conjugate (ADC) comprising the same toxin and a monoclonal antibody of the same isotype, same species, but directed against an irrelevant antigen.

Figure 1:
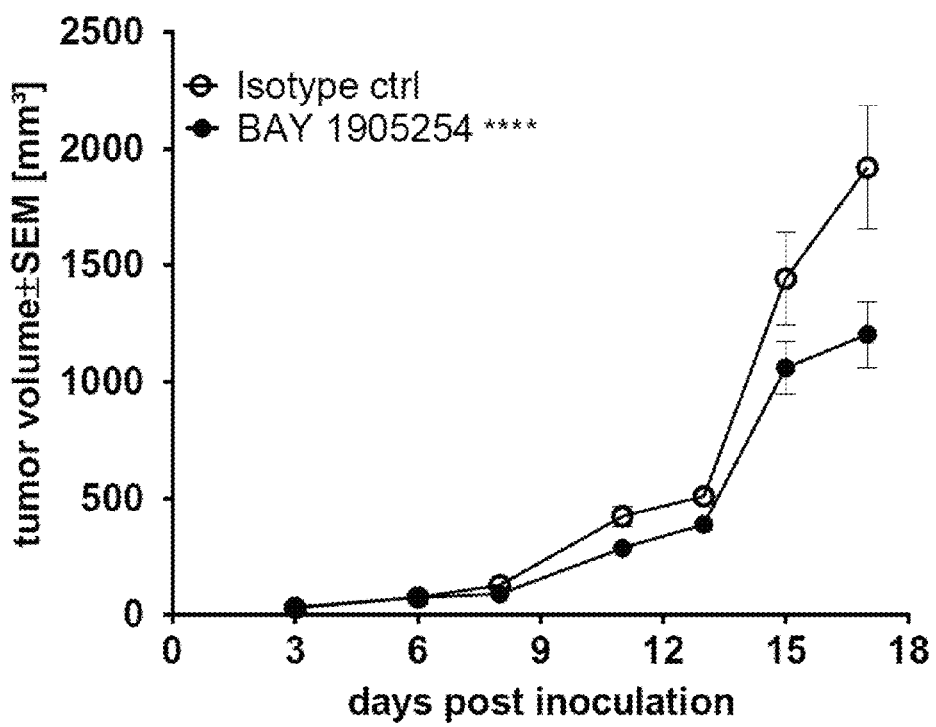

FIG. 1: Significance of BAY1905254 treatment compared to isotype control as determined by 2 way ANOVA analysis. The growth of B16F10 tumors was significantly delayed by treatment with BAY1905254 compared to isotype control. Start of treatment (d0). The experimental conditions are shown in the following table:

| Group No | N/group | Compound | Dose | Route | Application volume |
|---|---|---|---|---|---|
| Isotype control | 12 | Isotype hIgG2 | 20 mg/kg | i.p. | 5 ml/kg |
| aILDR2 | 12 | BAY1905254 | 10 mg/kg | i.p. | 5 ml/kg |
|  |  | Isotype hIgG2 | 10 mg/kg | i.p. | 5 ml/kg |

Figure 2:
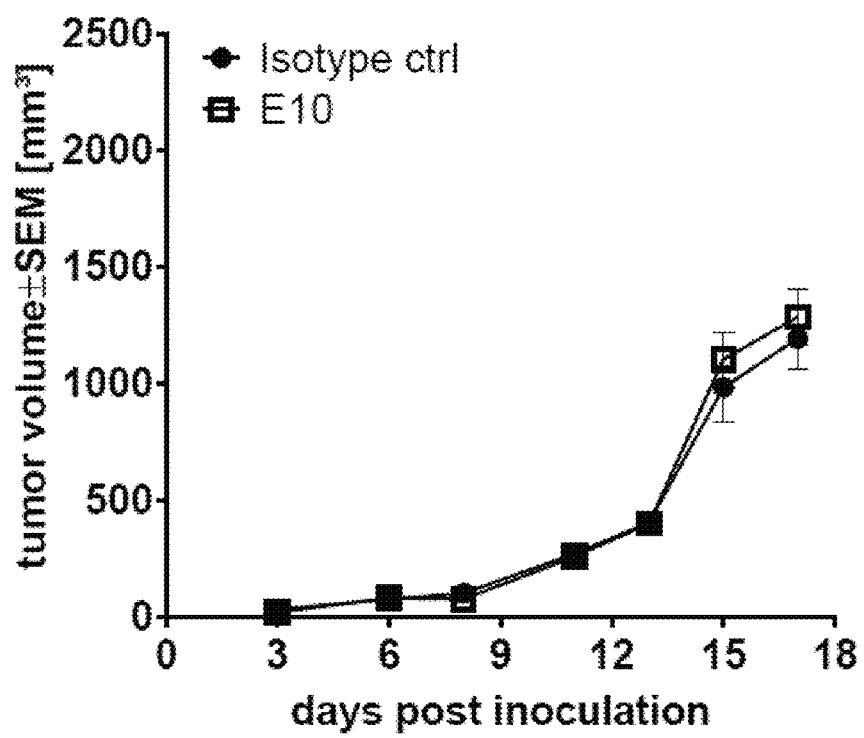

FIG. 2: Treatment with the E10 antibody did not affect growth of the B16F10 tumor model. Start of treatment (d0). The experimental conditions are shown in the following table:

| Group No | N/group | Compound | Dose | route | Application volume |
|---|---|---|---|---|---|
| Isotype control | 12 | Isotype hIgG2 | 10 mg/kg | i.p. | 5 ml/kg |
|  |  | Isotype mIgG1 | 10 mg/kg | i.p. | 5 ml/kg |
| E10 | 12 | E10 mIgG1 | 10 mg/kg | i.p. | 5 ml/kg |
|  |  | Isotype hIgG2 | 10 mg/kg | i.p. | 5 ml/kg |

Figure 3:
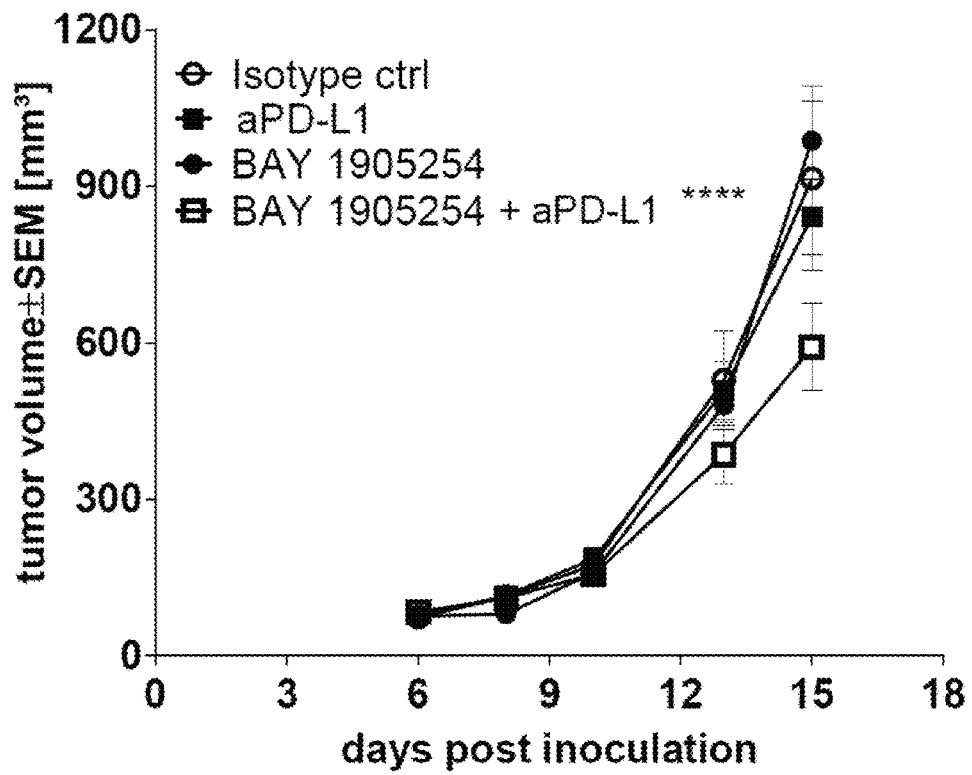

FIG. 3: Significance of monotherapy and combination treatment vs. isotype control as determined by 2 way ANOVA analysis. No monotherapy efficacy observed vs. isotype control neither with aPD-L1 nor with BAY1905254 treatment. Combination of aPD-L1 with BAY1905254 synergistically delayed tumor growth vs. control. Start of treatment: q3d i.p. The experimental conditions are shown in the following table:

| Group No | N/group | Compound | Dose | route | Application volume | Treatment schedule |
|---|---|---|---|---|---|---|
| Isotype control | 11 | Isotype hIgG2 | 20 mg/kg | i.p. | 5 ml/kg | Q3D |
|  |  | Isotype hamster hIgG1 | 10 mg/kg | i.p. | 5 ml/kg | Q3D |
| aPD-L1 | 11 | aPD-L1 | 10 mg/kg | i.p. | 5 ml/kg | Q3D |
|  |  | Isotype hIgG2 | 10 mg/kg | i.p. | 5 ml/kg | Q3D |
|  |  | Isotype hamster hIgG1 | 10 mg/kg | i.p. | 5 ml/kg | Q3D |
| aILDR2 | 11 | BAY1905254 | 10 mg/kg | i.p. | 5 ml/kg | Q3D |
|  |  | Isotype hIgG2 | 10 mg/kg | i.p. | 5 ml/kg | Q3D |
|  |  | Isotype hamster hIgG1 | 10 mg/kg | i.p. | 5 ml/kg | Q3D |
| aILDR2+ aPD-L1 | 11 | BAY1905254 | 10 mg/kg | i.p. | 5 ml/kg | Q3D |
|  |  | aPD-L1 | 10 mg/kg | i.p. | 5 ml/kg | Q3D |
|  |  | Isotype hamster hIgG1 | 10 mg/kg | i.p. | 5 ml/kg | Q3D |

Figure 4:
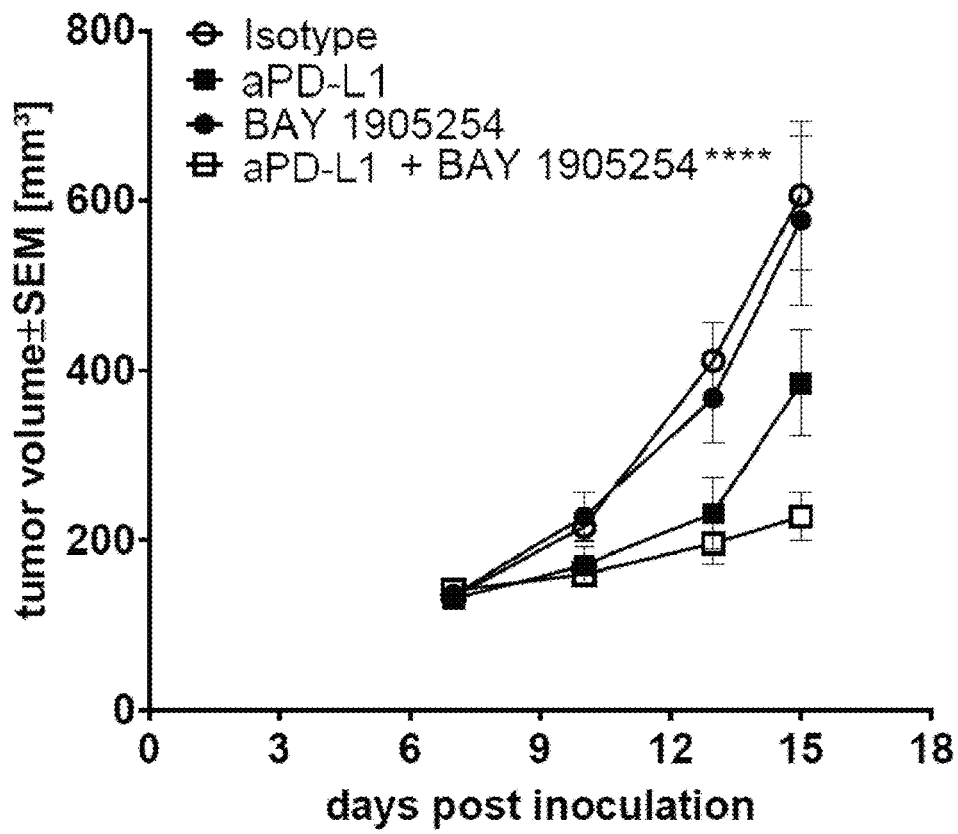

FIG. 4: Significance of aPD-L1 and BAY1905254 combination treatment compared to isotype control as determined by 2 way ANOVA analysis. BAY1905254 alone shows no delay of tumor growth at a dose of 3 mg/kg on the CT26 tumor model. At 10 mg/kg aPD-L1 shows efficacy vs. isotype control which is synergistically improved combining the 10 mg/kg aPD-L1 with 3 mg/kg BAY1905254. Start of treatment (d7): q3d i.p. The experimental conditions are shown in the following table:

| Group No | N/group | Compound | Dose | route | Application volume | Treatment schedule |
|---|---|---|---|---|---|---|
| Isotype control | 12 | Isotype hIgG2 | 40 mg/kg | i.p. | 5 ml/kg | Q3D |
| aPD-L1 | 12 | aPD-L1 | 10 mg/kg | i.p. | 5 ml/kg | Q3D |
|  |  | Isotype hIgG2 | 30 mg/kg | i.p. | 5 ml/kg | Q3D |
| aILDR2 | 12 | BAY1905254 | 3 mg/kg | i.p. | 5 ml/kg | Q3D |
|  |  | Isotype hIgG2 | 37 mg/kg | i.p. | 5 ml/kg | Q3D |
| aILDR2+ aPD-L1 | 12 | BAY1905254 | 3 mg/kg | i.p. | 5 ml/kg | Q3D |
|  |  | aPD-L1 | 10 mg/kg | i.p. | 5 ml/kg | Q3D |
|  |  | Isotype hIgG2 | 27 mg/kg | i.p. | 5 ml/kg | Q3D |

Figure 5:
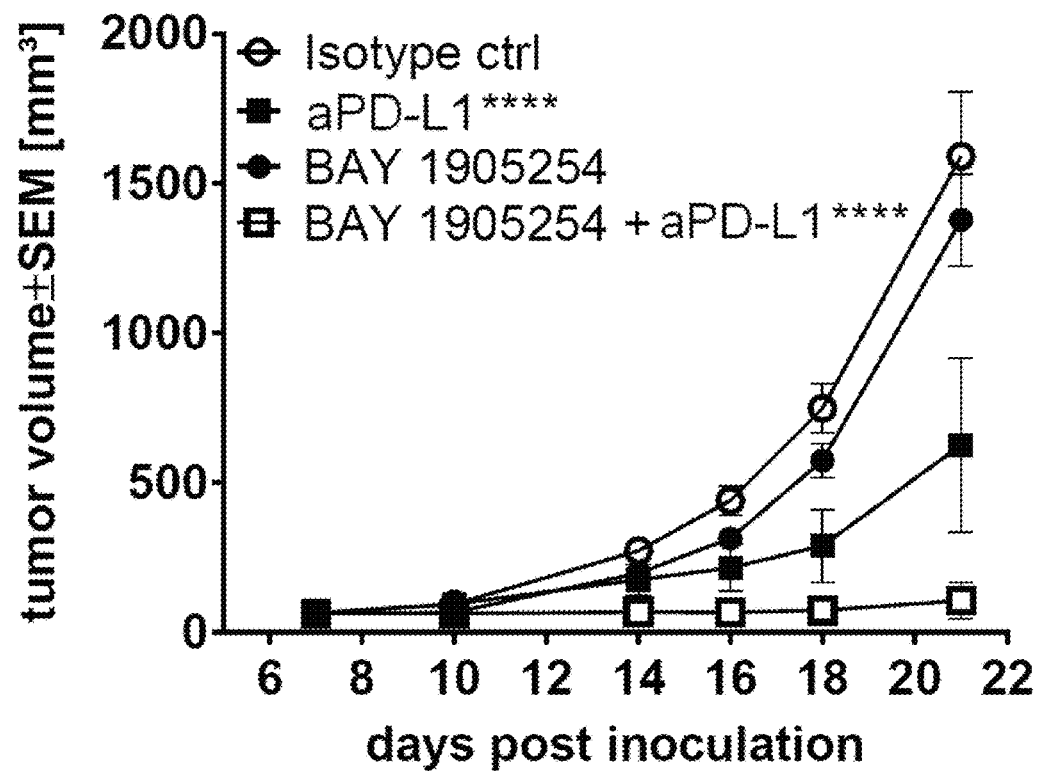

FIG. 5: Significance of monotherapy and combination treatment vs. isotype control as determined by 2 way ANOVA analysis. Treating the 3C9-D11-H11 model in monotherapy aPD-L1 achieves a significant delay of tumor growth vs. isotype control which is not the case for BAY1905254. Combining aPD-L1 with BAY1905254 shows synergy and prohibits outgrowth of the tumors. Start of treatment (d8): q3d i.p. The experimental conditions are shown in the following table:

| Group No | N/group | Compound | Dose | route | Application volume | Treatment schedule |
|---|---|---|---|---|---|---|
| Isotype control | 12 | Isotype hIgG2 | 20 mg/kg | i.p. | 5 ml/kg | Q3D |
| aPD-L1 | 12 | aPD-L1 | 10 mg/kg | i.p. | 5 ml/kg | Q3D |
|  |  | Isotype hIgG2 | 10 mg/kg | i.p. | 5 ml/kg | Q3D |
| aILDR2 | 12 | BAY1905254 | 10 mg/kg | i.p. | 5 ml/kg | Q3D |
|  |  | Isotype hIgG2 | 10 mg/kg | i.p. | 5 ml/kg | Q3D |
| aILDR2+ aPD-L1 | 12 | BAY1905254 | 10 mg/kg | i.p. | 5 ml/kg | Q3D |
|  |  | aPD-L1 | 10 mg/kg | i.p. | 5 ml/kg | Q3D |

Figure 6:
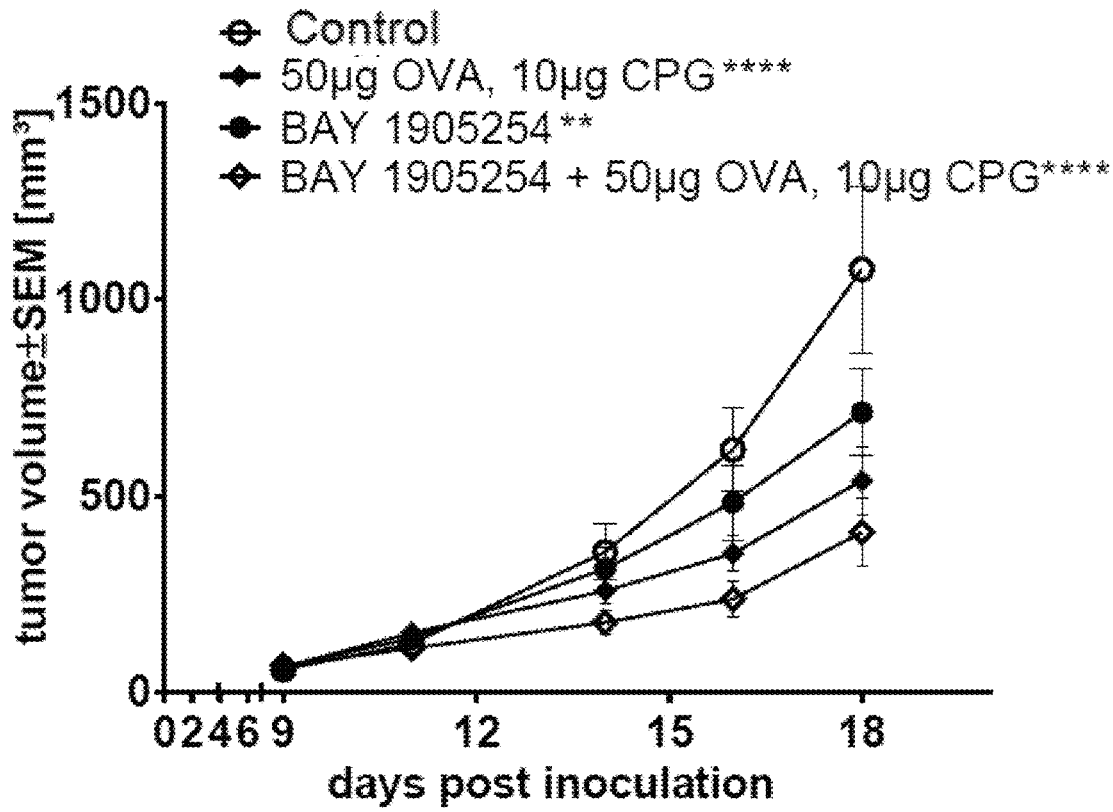

FIG. 6: Significance of monotherapy and combination treatment vs. isotype control as determined by 2 way ANOVA analysis. Treating the B16F10 OVA model in monotherapy BAY1905254 leads to a moderate delay of tumor growth. This is synergistically improved when BAY1905254 is combined with OVA and CPG. Start of treatment (d9): q3d i.p. The experimental conditions are shown in the following table:

| Group No | N/group | Compound | Dose | route | Application volume | Treatment schedule |
|---|---|---|---|---|---|---|
| Isotype control | 12 | Isotype hIgG2 | 20 mg/kg | i.p. | 5 ml/kg | Q3D |
| OVA/CpG | 12 | Isotype hIgG2 | 20 mg/kg | i.p. | 5 ml/kg | Q3D +OVA 50 μm/animal +CpG 10 μm/animal |
| aILDR2+ OVA/CpG | 12 | BAY1905254 | 10 mg/kg | i.p. | 5 ml/kg | Q3D +OVA 50 μm/animal +CpG 10 μm/animal |
|  |  | Isotype hIgG2 | 10 mg/kg | i.p. |  |  |
| aILDR2 | 12 | BAY1905254 | 10 mg/kg | i.p. | 5 ml/kg | Q3D |
|  |  | Isotype hIgG2 | 10 mg/kg | i.p. |  |  |

Figure 7:
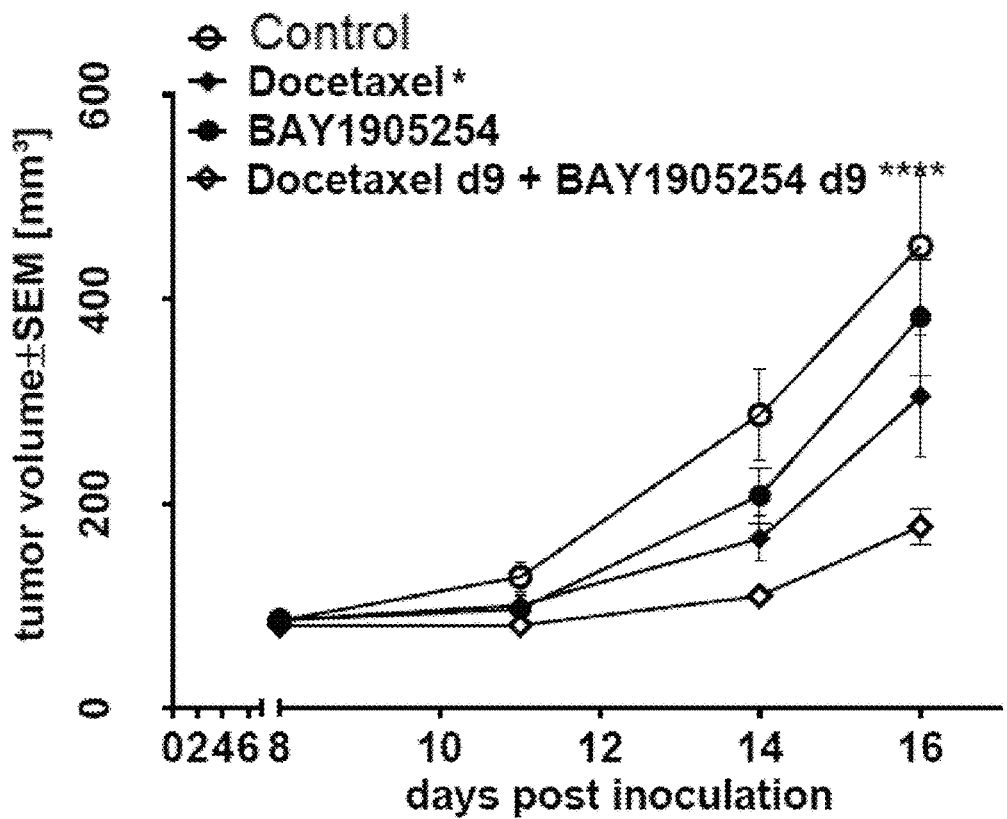

FIG. 7: Significance of monotherapy and combination treatment vs. isotype control as determined by 2 way ANOVA analysis. Treating the B16F10 OVA model in monotherapy BAY1905254 leads to a moderate delay of tumor growth. This is synergistically improved when BAY1905254 is combined with Docetaxel. Start of treatment (d8): q3d i.p. The experimental conditions are shown in the following table:

| Group No | N/group | Compound | Dose | route | Application volume | Treatment schedule |
|---|---|---|---|---|---|---|
| Isotype control | 12 | Isotype hIgG2 | 10 mg/kg | i.p. | 5 ml/kg | Q3D |
|  |  | Vehicle (isotonic NaCl; D-1) |  | c | 5 ml/kg | once |
| Docetaxel | 12 | Isotype hIgG2 | 10 mg/kg | i.p. | 5 ml/kg | Q3D |
|  |  | Docetaxel (D-1) | 20 mg/kg | i.v. | 5 ml/kg | once |
| aILDR2 | 12 | BAY1905254 | 10 mg/kg | i.p. | 5 ml/kg | Q3D |
|  |  | Vehicle (isotonic NaCl; D-1) |  | i.v. | 5 ml/kg | once |
| aILDR2+ Docetaxel | 12 | BAY1905254 | 10 mg/kg | i.p. | 5 ml/kg | Q3D |
|  |  | Docetaxel (D-1) | 20 mg/kg | i.v. | 5 ml/kg | once |

Figure 8:
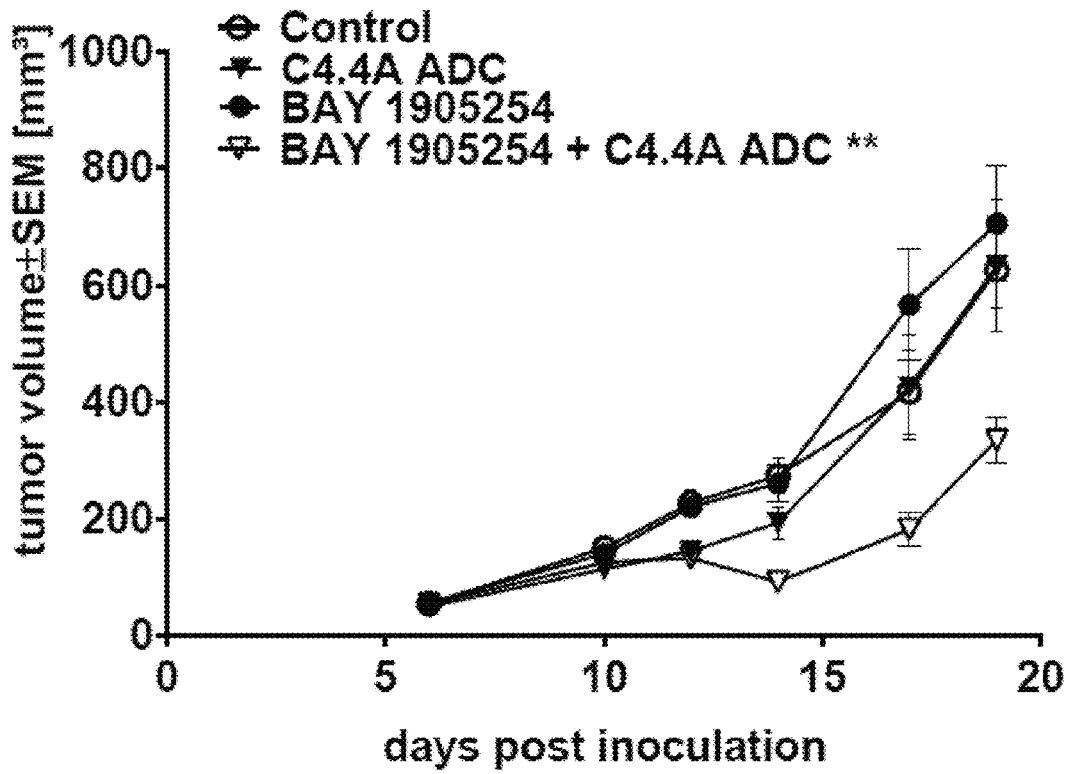

FIG. 8: Significance of monotherapy and combination treatment vs. isotype control as determined by 2 way ANOVA analysis. Treating the B16F10 OVA model in monotherapy BAY1905254 does not lead to a delay in tumor growth. A synergistic effect is yet visible when BAY1905254 is combined with C4.4a ADC. Start of treatment (d6): q3d i.p. The experimental conditions are shown in the following table:

| Group No | N/group | Compound | Dose | route | Application volume |
|---|---|---|---|---|---|
| Isotype control | 12 | Isotype hIgG2 | 10 mg/kg | i.p. | 10 ml/kg |
|  |  | Isotype ADC | 10 mg/kg | i.v. | 10 ml/kg |
| C4.4A ADC | 12 | C4.4A ADC | 10 mg/kg | i.v. | 10 ml/kg |
|  |  | Isotype hIgG2 | 10 mg/kg | i.p. | 10 ml/kg |
| aILDR2 | 12 | BAY1905254 | 10 mg/kg | i.p. | 10 ml/kg |
|  |  | Isotype ADC | 10 mg/kg | i.v. | 10 ml/kg |
| aILDR2 + C4.4A ADC | 12 | C4.4A ADC | 10 mg/kg | i.v. | 10 ml/kg |
|  |  | BAY1905254 | 10 mg/kg | i.p. | 10 ml/kg |

Figure 9A:
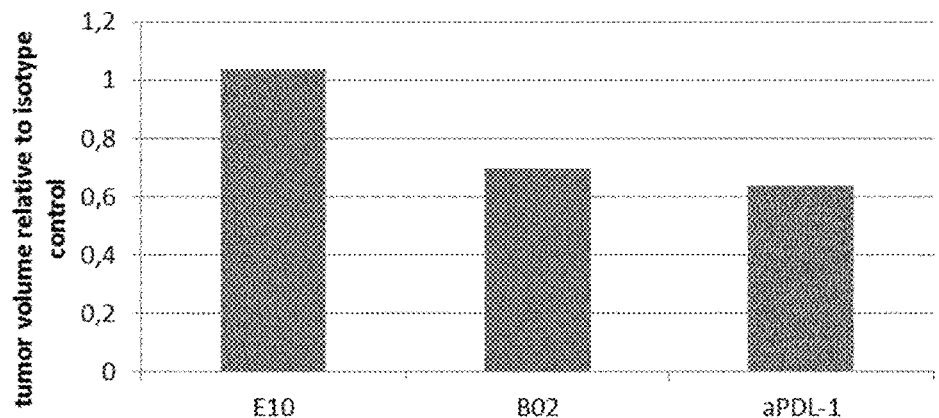

FIG. 9A: Tumor shrinking activity of different antibodies in a B16F10 syngeneic mouse model. Tumor shrinking activity is measured as decrease of tumor volume, relative to an isotype control.

Figure 9B:
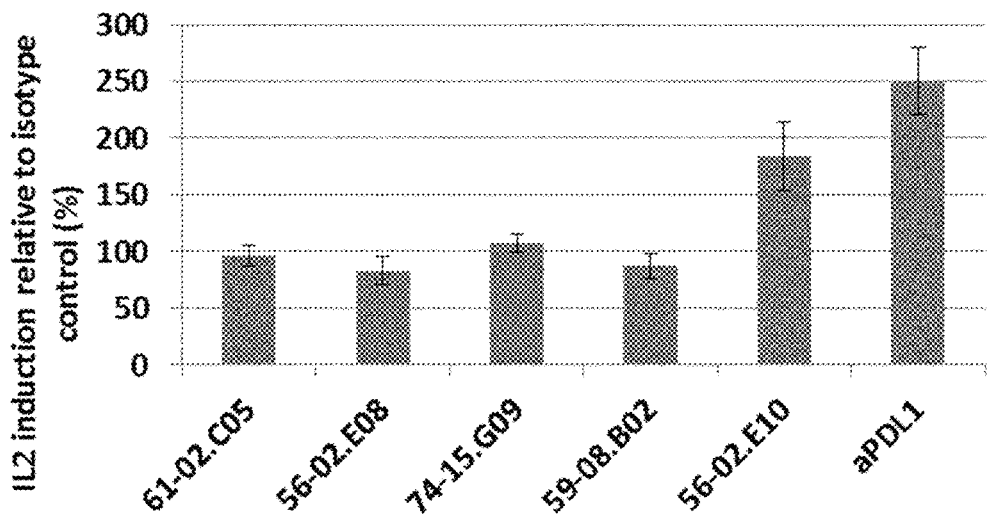

FIG. 9B: aberrant behavior of selected anti ILDR2 antibodies according to the present invention in an IL2 induction assay as compared to an anti PD-L1 antibody.

Figure 9C:
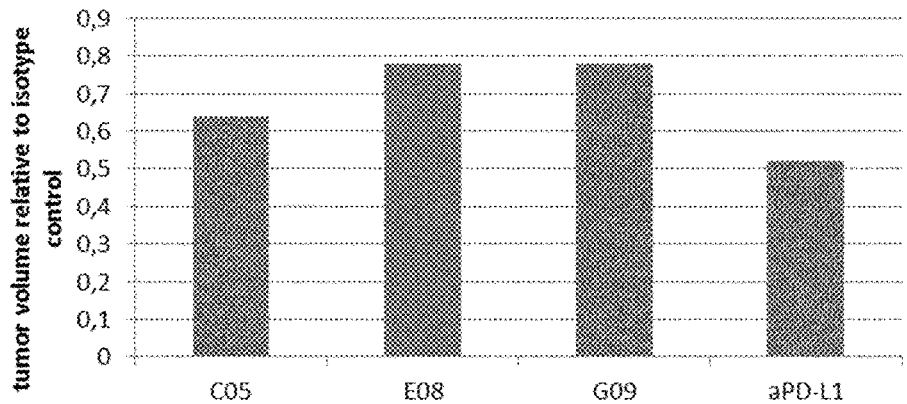

FIG. 9C: Tumor shrinking activity of selected anti ILDR2 antibodies according to the present invention in a CT26 syngeneic mouse model. Tumor shrinking activity is measured as decrease of tumor volume, relative to an Isotype control.

DEFINITIONS

Unless defined otherwise, all technical and scientific terms used herein have the meaning commonly understood by one of ordinary skill in the art to which this invention belongs. The following references, however, can provide one of skill in the art to which this invention pertains with a general definition of many of the terms used in this invention, and can be referenced and used so long as such definitions are consistent with the meaning commonly understood in the art. Such references include, but are not limited to, Singleton et al., Dictionary of Microbiology and Molecular Biology (2nd ed. 1994); The Cambridge Dictionary of Science and Technology (Walker ed., 1988); Hale & Marham, The Harper Collins Dictionary of Biology (1991); and Lackie et al., The Dictionary of Cell & Molecular Biology (3d ed. 1999); and Cellular and Molecular Immunology, Eds. Abbas, Lichtman and Pober, 2nd Edition, W. B. Saunders Company. Any additional technical resource available to the person of ordinary skill in the art providing definitions of terms used herein having the meaning commonly understood in the art can be consulted. For the purposes of the present invention, the following terms are further defined. Additional terms are defined elsewhere in the description. As used herein and in the appended claims, the singular forms "a," and "the" include plural reference unless the context clearly dictates otherwise.

"Amino acids" may be referred to herein by their commonly known three letter symbols or by the one-letter symbols recommended by the IUPAC-IUB Biochemical Nomenclature Commission. Nucleotides, likewise, may be referred to by their commonly accepted single-letter codes.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as an ILDR2 antagonist of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

"Antibodies", also synonymously called "immunoglobulins" (Ig), are generally comprising four polypeptide chains, two heavy (H) chains and two light (L) chains, and are therefore multimeric proteins, or an equivalent Ig homologue thereof (e.g., a camelid nanobody, which comprises only a heavy chain, single domain antibodies (dAbs) which can be either be derived from a heavy or light chain); including full length functional mutants, variants, or derivatives thereof (including, but not limited to, murine, chimeric, humanized and fully human antibodies, which retain the essential epitope binding features of an Ig molecule (or, if necessary, undergo affinity maturation or deiimuization), and including dual specific, bispecific, multispecific, and dual variable domain immunoglobulins.

Immunoglobulin molecules can be of any class (e.g., IgG, IgE, IgM, IgD, IgA, and IgY), or subclass (e.g., IgG1, IgG2, IgG3, IgG4, IgA1, and IgA2) and allotype. In one embodiment of present invention, the anti ILDR2 antibody is fully human and of the IgG2 subclass.

An "antibody-based binding protein", as used herein, may represent any protein that contains at least one antibody-derived $V_H$, $V_L$, or $C_H$ immunoglobulin domain in the context of other non-immunoglobulin, or non-antibody derived components. Such antibody-based proteins include, but are not limited to (i) $F_c$-fusion proteins of binding proteins, including receptors or receptor components with all or parts of the immunoglobulin $C_H$ domains, (ii) binding proteins, in which $V_H$ and or $V_L$ domains are coupled to alternative molecular scaffolds, or (iii) molecules, in which immunoglobulin $V_H$, and/or $V_L$, and/or $C_H$ domains are combined and/or assembled in a fashion not normally found in naturally occurring antibodies or antibody fragments.

An "antibody derivative or fragment", as used herein, relates to a molecule comprising at least one polypeptide chain derived from an antibody that is not full length, including, but not limited to (i) a Fab fragment, which is a monovalent fragment consisting of the variable light ($V_L$), variable heavy ($V_H$), constant light ($C_L$) and constant heavy 1 ($C_H1$) domains; (ii) a F(ab')2 fragment, which is a bivalent fragment comprising two Fab fragments linked by a disulfide bridge at the hinge region; (iii) a heavy chain portion of a $F_{ab}$ ($F_d$) fragment, which consists of the $V_H$ and $C_H1$ domains; (iv) a variable fragment ($F_v$) fragment, which consists of the $V_L$ and $V_H$ domains of a single arm of an antibody, (v) a domain antibody (dAb) fragment, which comprises a single variable domain; (vi) an isolated complementarity determining region (CDR); (vii) a single chain $F_v$ Fragment (scF$_v$); (viii) a diabody, which is a bivalent, bispecific antibody in which $V_H$ and $V_L$ domains are expressed on a single polypeptide chain, but using a linker that is too short to allow for pairing between the two domains on the same chain, thereby forcing the domains to pair with the complementarity domains of another chain and creating two antigen binding sites; and (ix) a linear antibody, which comprises a pair of tandem $F_v$ segments ($V_H$-$C_H1$-$V_H$-$C_H1$) which, together with complementarity light chain polypeptides, form a pair of antigen binding regions; and (x) other non-full length portions of immunoglobulin heavy and/or light chains, or mutants, variants, or derivatives thereof, alone or in any combination.

The term "modified antibody format", as used herein, encompasses antibody-drug-conjugates, Polyalkylene oxide-modified scFv, Monobodies, Diabodies, Camelid Antibodies, Domain Antibodies, bi- or trispecific antibodies, IgA, or two IgG structures joined by a J chain and a secretory component, shark antibodies, new world primate framework+non-new world primate CDR, IgG4 antibodies with hinge region removed, IgG with two additional binding sites engineered into the CH3 domains, antibodies with altered Fc region to enhance affinity for Fc gamma receptors, dimerised constructs comprising CH3+VL+VH, and the like.

The term "antibody mimetic", as used herein, refers to proteins not belonging to the immunoglobulin family, and even non-proteins such as aptamers, or synthetic polymers. Some types have an antibody-like beta-sheet structure. Potential advantages of "antibody mimetics" or "alternative scaffolds" over antibodies are better solubility, higher tissue penetration, higher stability towards heat and enzymes, and comparatively low production costs.

Some antibody mimetics can be provided in large libraries, which offer specific binding candidates against every conceivable target. Just like with antibodies, target specific antibody mimetics can be developed by use of High Throughput Screening (HTS) technologies as well as with established display technologies, just like phage display, bacterial display, yeast or mammalian display. Currently developed antibody mimetics encompass, for example, ankyrin repeat proteins (called DARPins), C-type lectins, A-domain proteins of *S. aureus*, transferrins, lipocalins, 10th type III domains of fibronectin, Kunitz domain protease inhibitors, ubiquitin derived binders (called affilins), gamma crystallin derived binders, cysteine knots or knottins, thioredoxin A scaffold based binders, nucleic acid aptamers, artificial antibodies produced by molecular imprinting of polymers, peptide libraries from bacterial genomes, SH-3 domains, stradobodies, "A domains" of membrane receptors stabilised by disulfide bonds and Ca2+, CTLA4-based compounds, Fyn SH3, and aptamers (oligonucleic acid or peptide molecules that bind to a specific target molecules)

The term "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

As used herein "ILDR2" relates to Immunoglobulin Like Domain Containing Receptor 2, also known as C1 ORF32, which is a novel member of the B7/CD28 family. For a thorough characterization of ILDR2, see WO2009032845, the content of which is incorporated by reference herein.

The terms "anti-ILDR2 antibody" and "an antibody that binds to ILDR2" refer to an antibody that is capable of binding ILDR2 with sufficient affinity such that the antibody is useful as a diagnostic and/or therapeutic agent in targeting ILDR2. In one embodiment, the extent of binding of an anti-ILDR2 antibody to an unrelated, non-ILDR2 protein is less than about 5%, or preferably less than about 2% of the binding of the antibody to ILDR2 as measured, e.g., by a surface plasmon resonance (SPR). In certain embodiments, an antibody that binds to ILDR2 has a dissociation constant (KD) of ≤1 µM, ≤100 nM, ≤10 nM, ≤1 nM, ≤0.1 nM, ≤0.01 nM, or ≤0.001 nM (e.g. 10-8 M or less, e.g. from 10-8 M to 10-13 M, e.g., from 10-9 M to 10-13 M). In certain embodiments, an anti-ILDR2 antibody binds to an epitope of ILDR2 that is conserved among ILDR2 from different species.

As used herein, the term "Complementarity Determining Regions" (CDRs; e.g., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (e.g. about residues 24-34 (L1), 50-56 (L2) and 89-97 (L3) in the light chain variable domain and 31-35 (H1), 50-65 (H2) and 95-102 (H3) in the heavy chain variable domain; (Kabat et al., Sequences of Proteins of Immulological Interest, 5th Ed. Public Health Service, National Institutes of Health, Bethesda, Md. (1991)) and/or those residues from a "hypervariable loop" (e.g. about residues 26-32 (L1), 50-52 (L2) and 91-96 (L3) in the light chain variable domain and 26-32 (H1), 53-55 (H2) and 96-101 (H3) in the heavy chain variable domain (Chothia and Lesk; J Mol Biol 196: 901-917 (1987)). In some instances, a complementarity determining region can include amino acids from both a CDR region defined according to Kabat and a hypervariable loop.

Depending on the amino acid sequence of the constant domain of their heavy chains, intact antibodies can be assigned to different "classes". There are five major classes of intact antibodies: IgA, IgD, IgE, IgG, and IgM, and several of these maybe further divided into "subclasses" (isotypes), e.g., IgG1, IgG2, IgG3, IgG4, IgA1, and IgA2. A preferred class of immunoglobulins for use in the present invention is IgG.

The heavy-chain constant domains that correspond to the different classes of antibodies are called [alpha], [delta], [epsilon], [gamma], and [mu], respectively. The subunit structures and three-dimensional configurations of different classes of immunoglobulins are well known. As used herein antibodies are conventionally known antibodies and functional fragments thereof.

Variants of the antibodies or antigen-binding antibody fragments contemplated in the invention are molecules in which the binding activity of the antibody or antigen-binding antibody fragment is maintained.

A "human" antibody or antigen-binding fragment thereof is hereby defined as one that is not chimeric (e.g., not "humanized") and not from (either in whole or in part) a non-human species. A human antibody or antigen-binding fragment thereof can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained there from. Another example of a human antibody or antigen-binding fragment thereof is one that is encoded by a nucleic acid isolated from a library of antibody sequences of human origin (e.g., such library being based on antibodies taken from a human natural source). Examples of human antibodies include antibodies as described in Söderlind et al., Nature Biotech. 2000, 18:853-856.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the term "monoclonal" indicates the character of the antibody as not being a mixture of discrete antibodies. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. The term "monoclonal" is not to be construed as to require production of the antibody by any particular method. The term monoclonal antibody specifically includes chimeric, humanized and human antibodies.

An "isolated" antibody is one that has been identified and separated from a component of the cell that expressed it. Contaminant components of the cell are materials that would interfere with diagnostic or therapeutic uses of the antibody, and may include enzymes, hormones, and other proteinaceous or nonproteinaceous solutes.

An "isolated" nucleic acid is one that has been identified and separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

As used herein, an antibody "binds specifically to", is "specific to/for" or "specifically recognizes" an antigen of interest, e.g. a tumor-associated polypeptide antigen target, is one that binds the antigen with sufficient affinity such that the antibody is useful as a therapeutic agent in targeting a cell or tissue expressing the antigen, and does not significantly cross-react with other proteins or does not significantly cross-react with proteins other than orthologs and variants (e.g. mutant forms, splice variants, or proteolytically truncated forms) of the aforementioned antigen target. The term "specifically recognizes" or "binds specifically to" or is "specific to/for" a particular polypeptide or an epitope on a particular polypeptide target as used herein can be exhibited, for example, by an antibody, or antigen-binding fragment thereof, having a monovalent KD for the antigen of less than about 10-4 M, alternatively less than about 10-5 M, alternatively less than about 10-6 M, alternatively less than about 10-7 M, alternatively less than about 10-8 M, alternatively less than about 10-9 M, alternatively less than about 10-10 M, alternatively less than about 10-11 M, alternatively less than about 10-12 M, or less. An antibody "binds specifically to," is "specific to/for" or "specifically recognizes" an antigen if such antibody is able to discriminate between such antigen and one or more reference antigen(s). In its most general form, "specific binding", "binds specifically to", is "specific to/for" or "specifically recognizes" is referring to the ability of the antibody to discriminate between the antigen of interest and an unrelated antigen, as determined, for example, in accordance with one of the following methods. Such methods comprise, but are not limited to surface plasmon resonance (SPR), Western blots, ELISA-, RIA-, ECL-, IRMA-tests and peptide scans. For example, a standard ELISA assay can be carried out. The scoring may be carried out by standard color development (e.g. secondary antibody with horseradish peroxidase and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative is more than 5-fold, 10-fold, 50-fold, and preferably more than 100-fold. Typically, determination of binding specificity is performed by using not a single reference antigen, but a set of about three to five unrelated antigens, such as milk powder, BSA, transferrin or the like.

"Binding affinity" or "affinity" refers to the strength of the total sum of non-covalent interactions between a single binding site of a molecule and its binding partner. Unless indicated otherwise, as used herein, "binding affinity" refers to intrinsic binding affinity which reflects a 1:1 interaction between members of a binding pair (e.g. an antibody and an antigen). The dissociation constant "KD" is commonly used to describe the affinity between a molecule (such as an antibody) and its binding partner (such as an antigen) i.e. how tightly a ligand binds to a particular protein. Ligand-protein affinities are influenced by non-covalent intermolecular interactions between the two molecules. Affinity can be measured by common methods known in the art, including those described herein.

As used herein, the term "epitope" includes any protein determinant capable of specific binding to an immunoglobulin or T-cell receptor. Epitopic determinants usually consist of chemically active surface groupings of molecules such as amino acids or sugar side chains, or combinations thereof and usually have specific three dimensional structural characteristics, as well as specific charge characteristics. An "antibody that binds to the same epitope" as a reference antibody or "an antibody which competes for binding" to a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "immunoconjugate" (interchangeably referred to as "antibody-drug conjugate," or "ADC") refers to an antibody conjugated to one or more cytotoxic or cytostatic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate) Immunoconjugates have been used for the local delivery of cytotoxic agents, i.e., drugs that kill or inhibit the growth or proliferation of cells, in the treatment of cancer (e.g. Liu et al., Proc Natl. Acad. Sci. (1996), 93, 8618-8623)) Immunoconjugates allow for the targeted delivery of a drug moiety to a tumor, and intracellular accumulation therein, where systemic administration of unconjugated drugs may result in unacceptable levels of toxicity to normal cells and/or tissues. Toxins used in antibody-toxin conjugates include bacterial toxins such as diphtheria toxin, plant toxins such as ricin, small molecule toxins such as geldanamycin. The toxins may exert their cytotoxic effects by mechanisms including tubulin binding, DNA binding, or topoisomerase inhibition.

"Percent (%) sequence identity" with respect to a reference polynucleotide or polypeptide sequence, respectively, is defined as the percentage of nucleic acid or amino acid residues, respectively, in a candidate sequence that are identical with the nucleic acid or amino acid residues, respectively, in the reference polynucleotide or polypeptide sequence, respectively, after aligning the sequences and introducing gaps, if necessary, to achieve the maximum percent sequence identity. Conservative substitutions are not considered as part of the sequence identity. Preferred are un-gapped alignments. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. "Sequence homology" indicates the percentage of amino acids that either is identical or that represent conservative amino acid substitutions.

"Neoplastic diseases" are conditions that cause tumor growth—both benign and malignant. A neoplasm is an abnormal growth of cells, also known as a tumor.

DETAILED DESCRIPTION OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a", "an", and "the" include singular and/or plural referents unless the context clearly dictates otherwise. It is moreover to be understood that, in case parameter ranges are given which are delimited by numeric values, the ranges are deemed to include these limitation values.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

Furthermore, the content of the prior art documents referred to herein is incorporated by reference. This refers, particularly, for prior art documents that disclose standard or routine methods. In that case, the incorporation by reference has mainly the purpose to provide sufficient enabling disclosure, and avoid lengthy repetitions.

According to one aspect of the invention, a pharmaceutical combination is provided comprising an ILDR2 antagonist plus optionally one or more other therapeutically active compounds.

Preferably, the ILDR2 antagonist of present invention is an anti ILDR2 antibody. More preferably, the anti ILDR2 antibody is an antibody as further described herein under.

According to one embodiment of the invention, the other therapeutically active compound is at least one selected from the group consisting of
a PD-L1 antagonist
a taxane or taxane derivative
a vaccine
a CpG oligodeoxynucleotide, and/or
a compound targeting c4.4A.

Preferably, the PD-L1 antagonist is an anti PD-L1 antibody. More preferably, the anti PD-L1 antibody comprises the variable domains of atezolizumab. Even more preferably, the anti PD-L1 antibody is atezoliuzumab.

The term "taxane derivative", as used herein, relates to cytotoxic or cytostatic compounds that comprise a taxadiene core. More preferably, the taxane derivative is paclitaxel, docetaxel or cabazitaxel.

The term "CpG oligodeoxynucleotide" refers to single-stranded synthetic DNA molecules that contain a cytosine triphosphate deoxynucleotide ("C") followed by a guanine triphosphate deoxynucleotide ("G"). The "p" refers to the phosphodiester link between consecutive nucleotides, although some ODN have a modified phosphorothioate (PS) backbone instead. When CpG motifs are unmethylated, they act as immunostimulants. In one embodiment, the CpG oligodeoxynucleotide is ODN1826 as e.g. distributed by Invivogen, having a nucleotide sequence of SEQ ID NO:17 (tccatgacgttcctgacgtt).

C4.4A (LYPD3, UniProtKB-095274 (LYPD3 HUMAN)) is an internalizing cell surface protein that has been identified as a cancer- and metastasis-associated surface marker. C4.4A (LYPD3) can hence be used as marker for targeting anti-cancer drugs to a tumor. The skilled person is capable, by routine methods, of generating compounds targeting C4.4A, e.g., by phage display or immunization, or by library screening with suitable screening methods. Hence, such compound targeting C4.4A can be an antibody, antibody fragment or derivative retaining target binding capacity, or an antibody mimetic. Further, such compound targeting c4.4A can be a small molecule.

In one embodiment the compound targeting C4.4A is an antibody drug conjugate comprising an antibody, or fragment or derivative thereof, or an antibody mimetic, targeting C4.4A, conjugated to a cytotoxic or cytostatic agent. Preferably, the compound targeting C4.4A is BAY1129980 which consists of an anti-C4.4A (LYPD3) antibody conjugated to Auristatin.

The present invention also provides antibody-drug conjugates (ADC, immunoconjugates) comprising an anti-ILDR2 antibody conjugated to one or more cytotoxic agents, such as chemotherapeutic agents or drugs, growth inhibitory agents, toxins (e.g., protein toxins, enzymatically active toxins of bacterial, fungal, plant, human or animal origin, or fragments thereof), or radioactive isotopes. Preferably, the anti-ILDR2 antibody is one as described herein under, most preferable the anti-ILDR2 antibody is BAY1905254.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP0425235); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof; an anthracycline such as daunomycin or doxorubicin; methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alphasarcin, *Aleurites fordii* proteins, dianthin proteins, Phytolaca americana proteins (P API, P APII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include 227Th, 225Ac, 211At, 1311, 1251, 90Y, 186Re, 188Re, 153Sm, 212Bi, 32P, 212Pb and radioactive isotopes of Lu. When the radioconjugate is used for detection, it may comprise a radioactive atom for scintigraphic studies, for example Tc99m, or a spin label for nuclear magnetic resonance (NMR) imaging, such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52: 12 7-131 (1992).

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

According to one embodiment of the invention, the ILDR2 antagonist and the other therapeutically active compound are:
provided in the same dosage unit, or
provided in individual dosage units.

According to one other embodiment of the invention, the ILDR2 antagonist and the other therapeutically active compound are:
administered simultaneously, or
administered sequentially, i.e., one after the other.

According to one embodiment of the invention, the ILDR2 antagonist is an antibody, a fragment or derivative thereof, a modified antibody format, or an antibody mimetic, all of which having ILDR2 binding properties.

According to one further aspect of the invention, an anti ILDR2 antibody, or a fragment or derivative thereof, or a modified antibody format, all of which having ILDR2 binding properties, is provided, which comprises at least the three CDR heavy chain sequences:
SEQ ID NO:1 CDR1 HC
SEQ ID NO:2 CDR2 HC
SEQ ID NO:3 CDR3 HC According to one further aspect of the invention, an anti ILDR2 antibody, or a fragment or derivative thereof, or a modified antibody format, all of which having ILDR2 binding properties, is provided, which comprises at least the three CDR light chain sequences:
SEQ ID NO:4 CDR1 LC
SEQ ID NO:5 CDR2 LC
SEQ ID NO:6 CDR3 LC Therein, "HC" stands for heavy chain and "LC" stands for light chain. The above sequences are the CDRs of BAY1905254 (also called 59-08.B02 herein).

According to one embodiment, the anti ILDR2 antibody, fragment or derivative or modified antibody format comprises at least one heavy chain or light chain variable region sequence that is 95% identical, preferably 96 or even 97% identical, more preferably 98% or even 99% identical, and most preferably 100% to a sequence selected from the group consisting of:
SEQ ID NO:7 HC VD
SEQ ID NO:8 LC VD Therein, "VD" stands for variable domain. The above sequences are the variable domains of BAY1905254 (synonymously called 59-08.B02 or B02 herein).

According to a further embodiment, the anti ILDR2 antibody, fragment or derivative or modified antibody format comprises at least one heavy chain or light chain sequence that is 95% identical, preferably 96% or even 97% identical, more preferably 98% or even 99% identical, and most preferably 100% to a sequence selected from the group consisting of:
SEQ ID NO:42 HC
SEQ ID NO:43 LC.

Therein, "HC" stands for heavy chain and "LC" stands for light chain. The above sequences are the heavy chain and light chain sequences of BAY1905254 (also called 59-08.B02 herein).

According to one further aspect of the invention, an anti ILDR2 antibody, or a fragment or derivative thereof, or a modified antibody format, all of which having ILDR2 binding properties, is provided, which comprises at least one combination of three CDR heavy chain sequences, selected from a group consisting of:
SEQ ID NO:18-20, 61-02.C05
SEQ ID NO:24-26, 56-02.E08
SEQ ID NO:30-32, and/or 74.15.G09
SEQ ID NO:36-38. 56.02.E10

According to one further aspect of the invention, an anti ILDR2 antibody, or a fragment or derivative thereof, or a modified antibody format, all of which having ILDR2 binding properties is provided, which comprises at least one combination of three CDR light chain sequences selected from a group consisting of:
SEQ ID NO:21-23, 61-02.C05
SEQ ID NO:27-29, 56-02.E08
SEQ ID NO:33-35 and/or 74.15.G09
SEQ ID NO:39-41. 56.02.E10

The above sequences are the CDRs of the antibodies 61-02.005, 56-02.E08, 74.15.G09 and 56.02.E10.

According to one further aspect of the invention, an anti ILDR2 antibody, or a fragment or derivative thereof, or a modified antibody format, all of which having ILDR2 binding properties, is provided, which comprises at least one heavy chain or light chain variable region sequence that is 95% identical, preferably 96 or even 97% identical, more preferably 98% or even 99% identical, and most preferably 100% to a sequence selected from the group consisting of:
SEQ ID NO:9, 61-02.C05 HC VD
SEQ ID NO:10, 61-02.C05 LC VD
SEQ ID NO:11, 56-02.E08 HC VD
SEQ ID NO:12, 56-02.E08 LC VD
SEQ ID NO:13, 74.15.G09 HC VD
SEQ ID NO:14, 74.15.G09 LC VD
SEQ ID NO:15, and/or 56.02.E10 HC VD
SEQ ID NO:16. 56.02.E10 LC VD The above sequences are the variable domains of 61-02.005, 56-02.E08, 74.15.G09 and 56.02.E10.

According to a further embodiment of present invention an anti ILDR2 antibody, or a fragment or derivative thereof, or a modified antibody format, all of which having ILDR2 binding properties, is provided, which comprises at least one heavy chain or light chain sequence that is 95% identical, preferably 96 or even 97% identical, more preferably 98% or even 99% identical, and most preferably 100% to a sequence selected from the group consisting of:
SEQ ID NO:44,
SEQ ID NO:45,
SEQ ID NO:46,
SEQ ID NO:47,
SEQ ID NO:48,
SEQ ID NO:49,
SEQ ID NO:50, and/or
SEQ ID NO:51.

The following table shows an overview of these sequences, and the antibodies they belong to.

| SEQ ID No | Antibody + Type |
| --- | --- |
| 7 | B02 (= 59-08.B02) Heavy chain variable domain |
| 8 | B02 (= 59-08.B02) Light chain variable domain |
| 9 | C05 (= 61-02.005) Heavy chain variable domain |
| 10 | C05 (= 61-02.005) Light chain variable domain |
| 11 | E08 (= 56-02.E08) Heavy chain variable domain |
| 12 | E08 (= 56-02.E08) Light chain variable domain |
| 13 | G09 (= 74.15.G09) Heavy chain variable domain |
| 14 | G09 (= 74.15.G09) Light chain variable domain |
| 15 | E10 (= 56.02.E10) Heavy chain variable domain |
| 16 | E10 (= 56.02.E10) Light chain variable domain |
| 42 | B02 (= 59-08.B02) Heavy chain |
| 43 | B02 (= 59-08.B02) Light chain |
| 44 | C05 (= 61-02.005) Heavy chain |
| 45 | C05 (= 61-02.005) Light chain |
| 46 | E08 (= 56-02.E08) Heavy chain |
| 47 | E08 (= 56-02.E08) Light chain |
| 48 | G09 (= 74.15.G09) Heavy chain |
| 49 | G09 (= 74.15.G09) Light chain |
| 50 | E10 (= 56.02.E10) Heavy chain |
| 51 | E10 (= 56.02.E10) Light chain |

According to one embodiment of the invention, the ILDR2 antibody or fragment or derivative or modified antibody format is selected from the group consisting of 61-02.005, 56-02.E08, 74.15.G09 and 59-08.B02.

According to one embodiment of the invention, the ILDR2 antagonist or antibody, or fragment or derivative or modified antibody format dissociates from human ILDR2 with a $K_d$ of 25 nM ($2{,}5 \times 10^{-8}$ M) or less, determined by fluorescence-activated cell scanning (FACS).

Preferably, said $K_d$ is 15 nM or less. More preferably, said $K_d$ is 13 nM or less. More preferably, said $K_d$ is 11 nM or less. More preferably, said $K_d$ is 8 nM or less. More preferably, said $K_d$ is 5 nM or less. More preferably, said $K_d$ is 3 nM or less. Most preferably, said $K_d$ is 2 nM or less.

According to one further aspect of the invention, an ILDR2 antagonist or antibody, or fragment or derivative or modified antibody format is provided which competes for binding to ILDR2 with an ILDR2 antibody according to the above specification.

According to one other aspect of the invention, an isolated nucleic acid sequence, or a set thereof, is provided that encodes an ILDR2 antibody, or fragment or derivative or modified antibody format according to the above specification.

According to one other aspect of the invention, a vector comprising at least one nucleic acid sequence according to the above specification is provided.

According to one other aspect of the invention, an isolated cell expressing an ILDR2 antibody, or fragment or derivative or modified antibody format according to the above specification and/or comprising a nucleic acid sequence, or a set thereof according to the above specification, or a vector according to the above specification is provided.

According to one embodiment of the invention, the pharmaceutical combination comprises the ILDR2 antagonist or antibody, or fragment or derivative or modified antibody format according to the above specification.

Therapeutic Methods

Therapeutic methods involve administering to a subject in need of treatment a therapeutically effective amount of an antibody or an antigen-binding fragment thereof or a variant thereof contemplated by the invention. A "therapeutically effective" amount hereby is defined as the amount of an antibody or antigen-binding fragment that is of sufficient quantity, either as a single dose or according to a multiple dose regimen, alone or in combination with other agents, to lead to the alleviation of an adverse condition, yet which amount is toxicologically tolerable. The subject may be a human or non-human animal (e.g., rabbit, rat, mouse, dog, monkey or other lower-order primate).

According to one other aspect of the invention, the ILDR2 antagonist or antibody, or fragment or derivative or modified antibody format, or the combination comprising an ILDR2 antagonist according to the above specification, is provided for use as a medicament.

It is an embodiment of the invention to provide an antibody or antigen-binding fragment thereof for use as a medicament for the treatment of cancer.

According to one embodiment, the ILDR2 antagonist or antibody, or fragment or derivative or modified antibody format, or the combination comprising an ILDR2 antagonist is for use in the treatment of a patient that is
　suffering from,
　at risk of developing, and/or
　being diagnosed for
a neoplastic disease, such as cancer, or an immune disease or disorder, wherein the ILDR2 antagonist is administered in one or more therapeutically efficient dosages.

According to one other embodiment, a method for treating a patient
　suffering from,
　at risk of developing, and/or
　being diagnosed for
a neoplastic disease, such as cancer, or an immune disease or disorder, is provided, said method comprising administering to said patient an ILDR2 antagonist or antibody, or fragment or derivative or modified antibody format, or a combination comprising an ILDR2 antagonist, according the above specification, in one or more therapeutically efficient dosages.

It is a further embodiment of the invention to use the antibody or antigen-binding fragment thereof in the manufacture of a medicament for the treatment of cancer.

The inventive antibodies or antigen-binding fragments thereof can be used as a therapeutic or a diagnostic tool in a variety of situations with aberrant ILDR2-signaling, e.g. cell proliferative disorders such as cancer. Disorders and conditions suitable for treatment with an antibody of the inventions can be, but are not limited to solid tumors, such as for example cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Tumors of the digestive tract include, but are not limited to anal, colon, colorectal, esophageal, gallbladder, gastric, pancreatic, rectal, small-intestine, and salivary gland cancers.

Examples of esophageal cancer include, but are not limited to esophageal cell carcinomas and Adenocarcinomas, as well as squamous cell carcinomas, Leiomyosarcoma, Malignant melanoma, rhabdomyosarcoma and Lymphoma.

Examples of gastric cancer include, but are not limited to intestinal type and diffuse type gastric adenocarcinoma.

Examples of pancreatic cancer include, but are not limited to ductal adenocarcinoma, adenosquamous carcinomas and pancreatic endocrine tumors.

Examples of breast cancer include, but are not limited to triple negative breast cancer, invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal and vulvar cancer, as well as sarcoma of the uterus.

Examples of ovarian cancer include, but are not limited to serous tumour, endometrioid tumor, mucinous cystadenocarcinoma, granulosa cell tumor, Sertoli-Leydig cell tumor and arrhenoblastoma.

Examples of cervical cancer include, but are not limited to squamous cell carcinoma, adenocarcinoma, adenosquamous carcinoma, small cell carcinoma, neuroendocrine tumour, glassy cell carcinoma and villoglandular adenocarcinoma.

Tumors of the urinary tract include, but are not limited to bladder, penile, kidney, renal pelvis, ureter, urethral, and hereditary and sporadic papillary renal cancers.

Examples of kidney cancer include, but are not limited to renal cell carcinoma, urothelial cell carcinoma, juxtaglomerular cell tumor (reninoma), angiomyolipoma, renal oncocytoma, Bellini duct carcinoma, clear-cell sarcoma of the kidney, mesoblastic nephroma and Wilms' tumor.

Examples of bladder cancer include, but are not limited to transitional cell carcinoma, squamous cell carcinoma, adenocarcinoma, sarcoma and small cell carcinoma.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct car-cinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to squamous cell cancer of the head and neck, laryngeal, hypopharyngeal, nasopharyngeal, oropharyngeal cancer, salivary gland cancer, lip and oral cavity cancer, and squamous cell cancer.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

In addition, the inventive antibodies or antigen-binding fragments thereof can also be used as a therapeutic or a diagnostic tool in a variety of other disorders wherein ILDR2 is involved.

EXAMPLES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

All amino acid sequences disclosed herein are shown from N-terminus to C-terminus; all nucleic acid sequences disclosed herein are shown 5'→3'.

1. Tumor Mouse Models

The following syngeneic tumor models were subcutaneously used in in vivo experiments: B16-F10 cells represent a mouse melanoma cell line derived from the skin of C57BL/6J mice. CT26 is an N-nitroso-N-methylurethane-(NNMU) induced, undifferentiated colon carcinoma cell line. It is a fibroblast cell type and derives from BALB/c mice. 3C9-D11-H11 cells are hybridoma B lymphocytes generated by fusion of spleen cells with Sp2/0-Ag14 myeloma cells. The spleen cells derive from BALB/c mice that were immunized with purified porcine parvovirus (PPV).

2. Antibody Generation

Antibodies against ILDR2 were generated by phage display. Briefly, panning reactions were carried out in solution using streptavidin-coated magnetic beads to capture the biotinylated antigens. Beads were recovered using a magnetic rack (Promega). All phage panning experiments used the X0MA031 human fab antibody phage display library (XOMA Corporation, Berkeley, Calif.) blocked with 5% skim milk.

Proteins required for phage display were biotinylated using a Sulfo-NHS-LC-Biotin kit (Pierce). Free biotin was removed from the reactions by dialysis against the appropriate buffer. The biotin labelled proteins included ILDR2-HM and the ECD of a control antigen fused to the same mouse $IgG_{2a}$ sequence. The control antigen was used for depletion steps in panning experiments. It was necessary to remove unwanted binders to streptavidin beads and the mouse $IgG_{2a}$ Fc domain during the panning process. To achieve this, streptavidin beads were coupled with the control antigens. A phage aliquot was then mixed with these 'depletion' beads and incubated at room temperature (RT) for 30 mins. The depletion beads were then discarded. For selection of specific binders to ILDR2-HM, the blocked and depleted phage library was mixed with magnetic beads coupled to biotinylated ILDR2-HM. Reactions were incubated at RT for 1-2 hrs and non-specific phage were removed by washing with PBS-T and PBS. After washing, bound phage were eluted by incubation with 100 mM triethylamine (EMD) and the eluate was neutralized by adding Tris-HCl pH 8.0 (Teknova). The resulting E. coli lawns were scraped and re-suspended in liquid growth media. A small aliquot of re-suspended cells was inoculated into a 100 mL culture (2YT with and ampicillin) and grown at 37° C. until the OD at 600 nM reached 0.5. This culture was infected with M13K07 helper phage (New England Biolabs) and kanamycin was added (selection antibiotic for M13K07). The culture was then maintained at 25° C. to allow phage packaging. An aliquot of the culture supernatant was carried over for either a subsequent round of panning or fab binding screens. Second and later rounds were conducted the same way, except that the rescued phage supernatant from the previous round was used in place of the phage library. The phage eluate was infected into TG1 E. coli, which transformed the cells with the X0MA031 phagemid. Transformed cells were then spread on selective agar plates (ampicillin) and incubated overnight at 37° C. The X0MA031 library is based on phagemid constructs that also function as IPTG inducible fab expression vectors. Eluted phage pools from panning round 3 were diluted and infected into TG1 E. coli cells (Lucigen) so that single colonies were generated when spread on an agar plate. Individual clones were grown in 1 mL cultures (2YT with glucose and ampicillin) and protein expression was induced by adding IPTG (Teknova). Expression cultures were incubated overnight at 25° C. Fab proteins secreted into the E. coli periplasm were then extracted for analysis. Each plate of samples also included duplicate 'blank PPE' wells to serve as negative controls. These were created from non-inoculated cultures processed the same way as the fab PPEs. FACS analyses were used to identify fabs with affinity for ILDR2. Individual fab PPEs were tested for binding to HEK-293T cells over-expressing human ILDR2 (293T-huILDR2 cells). All analyses included negative control HEK-293T cells mock transfected with an 'empty vector' control plasmid (293T-EV cells). Reagent preparation and wash steps were carried out in FACS buffer (PBS with 1% BSA). Fab and blank PPEs were mixed with an aliquot of cells, incubated for 1 hr at 4° C. and then washed with FACS buffer. Cells were then mixed with an anti-C-myc primary antibody (Roche). After the same incubation and wash step cells were stained with an anti-mouse IgG Fc AlexaFlour-647 antibody (Jackson Immunoresearch). After a final incubation and wash cells were fixed in 4% paraformaldehyde made up in FACS buffer. Samples were read on a HTFC screening system (Intellicyt). Data was analyzed using FCS Express (De Novo Software, CA, USA) or FloJo (De Novo Software, CA, USA). Based on these results, five binders were chosen for further analysis and reformatted into full length IgGs.

TABLE 1

Antibodies used in the present study

| Alias Name | Full Name |
|---|---|
| B02 | 59-08.B02 |
| C05 | 61-02.005 |
| E08 | 56-02.E08 |
| G09 | 74.15.G09 |
| E10 | 56.02.E10 |

As a comparison, an anti PD-L1 antibody was used in some experiments. The anti-PD-L1 antibody (also called aPDL1 herein) is a chimera of the variable domain of atezolizumab with human IgG2 domains.

3. Antibody Production

These IgGs were expressed and purified using standard procedures. Briefly, IgGs were produced by mammalian cell culture using transiently transfected HEK293-6E cells. Heavy and light chain were cloned into a pTT5 Dual vector system. Cell culture scale was 4×1.5 l in shake flask utilizing F17 medium (Life Technologies; supplemented with 0.1% pluronic F68 (Life Technologies) and 4 mM Glutamax (Life Technologies)). 24 h post-transfection, 1% FCS "ultra low" IgG (Life Technologies) and 0.5 mM valproic acid (Sigma Aldrich) were added. 6.0 l cell supernatant was filter-sterilized and stored at 4° C. prior to purification. IgGs were purified using a standard purification protocol. Capture step is affinity chromatography on MabSelect SuRe followed by preparative SEC on Superdex 200. The filtered (0.2 µm) supernatants from HEK-293 cells were directly loaded onto a MabSelect SuRe column (200 ml) using AEKTA Explorer 100 System (GE-Healthcare). After elution from the $1^{st}$ column, Peak fractions were pooled and neutralized using 3.0 M Tris pH 9. After sterile filtration, the filtrate was stored at 4° C. until SEC. A single injection was performed on Superdex 200 prep grade XK 50/100 (column volume ~1.8 L) with the same Chromatography System.

Peaks were pooled. Final IgG containing fractions were concentrated to about 10 mg/ml using Amicon ultra-15 concentration devices (Millipore, 30 kDa MWCO). Protein amount and concentration were determined by Nanodrop UV spectrophotometer; samples were sterile filtered, aliquoted, frozen in liquid nitrogen and stored at −80° C.

4. Characterization of Antigen Binding of Selected Antibodies $K_D$ values were determined by flowcytometric quantitation of binding to HEK cells stably transfected with human ILDR2 and use of an algorithm designed to extrapolate affinities based on the binding curve. Briefly, hIgG1 s were added at a binding site concentration range of 3 pM-209 nM to a constant number of cells (100,000 cells/well) over 16 wells in a 96-well plate. One well contained cells without any added IgG to serve as a blank well. The cells were equilibrated for 4 hours at 4° C. An excess of Cy5-labeled goat anti-human polyclonal antibody (Jackson ImmunoResearch 109-606-097) at 90 nM was added to each well after one FACS buffer wash of the cells. Cells were washed twice after a 30 minute incubation (at 4° C.) with the labeling pAb and then the Mean Fluorescence Intensity (MFI) was recorded over approximately 10,000 "events" using an Intellicyte flow cytometer. The $K_m$s of the IgGs binding to HEK 293 cells expressing ILDR2 were estimated by fitting the MFI vs. the IgG binding site concentration curve using a 1:1 equilibrium model as detailed in Drake and Klakamp (2007). Experiments carried out with HEK cells expressing murine ILDR2 yielded comparable binding. Control experiments using untransfected cells demonstrated that binding was strictly ILDR2-dependent. Results are shown in the following table 2.

TABLE 2

Dissociation constants of antibodies according to the present invention

| Binder | Kd (nM) |
|---|---|
| B02 | 2.0 |
| C05 | 10.7 |
| E08 | 2.7 |
| G09 | 12.4 |

5. Anti-Tumor Efficacy, Such as for Example, Shrinking Activity of Selected Binders in Syngeneic in Vivo Mouse Models To determine the anti-tumor efficacy, such as for example, the tumor shrinking effect of the respective binders, two syngeneic mouse models (B16F10, CT26) were used as discussed above. It turned out that, when measured against an isotype control, the anti ILDR2 antibody E10 shows no tumor shrinkage at all, while the anti PD-L1 antibody and the anti ILDR2 antibody B02 do (see FIG. 9A).

6. Modulation of ILDR2 Activity by Selected Binders in MLR

To determine the effect of these antibodies on ILDR2 function an immunomodulation assay was carried out, namely a mixed lymphocyte reaction assay. The mixed lymphocyte reaction (MLR) is a test in which populations of lymphocytes are mixed together, and the resulting reactions are measured. Technically, it is an ex-vivo cellular immune assay that occurs between two allogeneic lymphocyte populations. In a one-way MLR, only one lymphocyte population can respond or proliferate. In a two-way MLR, both populations can proliferate. MLR's are performed to assess how T cells react to external stimuli, e.g., exposure to immune checkpoint inhibitors, like anti PD-1 antibodies (Wang et al 2014) and anti-PD-L1 antibodies. In the present context, antibody-evoked IL-2 secretion was measured with this assay.

In the present case, CD4 T cells from one donor were co-cultured with M-CSF mature monocytes from another donor in the presence of various ILDR2 antibodies, a function-blocking PD-L1 antibody or an isotype control for 5 days. Supernatants were harvested and the concentration of ILDR2, a classical T cell activation marker, was determined by Elisa. As expected, the anti PD-L1 antibody induced a significant increase in IL-2 secretion over isotype control. One ILDR2 antibody, E10, had a comparable effect. Results are shown in FIG. 9B and the following table 3.

TABLE 3

IL2 induction of selected antibodies

| Binder | IL2 concentration (% over isotype control) |
|---|---|
| aPDL1 | 247 +/− 21 |
| B02 | 91 +/− 11 |
| C05 | 82 +/− 9 |
| E08 | 74 +/− 12 |
| G09 | 86 +/− 8 |
| E10 | 223 +/− 30 |

This prompted the inventors to test those further anti ILDR2 antibodies that, just like B02, do not mediate IL-2 induction in the MLR, in further in vivo models. It turned out that in a CT26 model, the antibodies G09, E08, B02 and C05 show similar anti-tumor efficacy when measured against an isotype control (see FIG. 9C). Hence, quite surprisingly, the anti ILDR2 antibodies G09, E08, B02 and C05 have cytokine induction activity in an immunomodulation assay which is lower than that of the anti PD-L1 antibody, but show anti-tumor activity in an in vivo tumor model which is comparable to that of an anti PD-L1 antibody.

In the IL-2-secretion assay, only one anti-ILDR2 antibody, namely E10, showed a similar behavior as a comparative anti PD-L1 antibody—yet was inactive in an in vivo assay. The remaining anti-ILDR2 antibodies tested did not trigger IL-2 secretion, but, nonetheless, proved active in in vivo assays. Hence, the inventors conclude that IL-2-secretion assays are not predictive for in vivo activity of anti-ILDR2 antibodies. Rather, it appears that the epitope space delineated by the anti-ILDR2 antibodies demonstrated to have in vivo activity delineates an epitope space suitable for the generation of ILDR2 antibodies with in vivo anti-tumor activity and, hence, with therapeutic potential.

In an assay in which the cytokine induction activity is measured as secretion of IL-2, TNFα, IL-6 and/or IFN-γ, relative to an Isotype control,
- the IL-2 induction of a preferred ILDR2 antagonist is ≤40% compared to that of an anti PD-L1 antibody
- the TNFα induction of a preferred ILDR2 antagonist is ≤28% compared to that of an anti PD-L1 antibody
- the IL-6 induction of a preferred ILDR2 antagonist is ≤50% compared to that of an anti PD-L1 antibody
- the IFNγ induction of a preferred ILDR2 antagonist is ≤68% compared to that of an anti PD-L1 antibody.

7. In Vivo Experiments with B02 (BAY1905254)

The anti-PD-L1 (also called aPDL1 herein) antibody is a chimera of the variable domain of atezolizumab with human IgG2 domains. BAY1905254 (also called aILDR2 herein) consists out of a variable domain binding the extracellular domain of ILDR2 and a constant domain framework. Both, aPD-L1 and aILDR2 are controlled in in vivo experiments by a human IgG2 isotype control. E10 consists out of a variable domain binding the extracellular domain of ILDR2 and a constant domain framework, and is controlled in in vivo experiments by a murine IgG1 isotype control.

All animal experiments were performed under German Animal Welfare Law and approved by local authorities.

7.1. B16-F10 Preventive Treatment

Eight weeks old female C57B1/6N Crl BR mice (body weight 18-20 g) from Charles River Deutschland, Sulzfeld were used for the B16F10 tumor model. The experiment was initiated after an acclimatization period of 8 days. Animals were kept in a 12-hour light/dark cycle. Food and water was available ad libitum. Housing temperature was maintained at 21° C. Mice (n=12 per group) were s.c. inoculated with $1 \times 10^4$ B16-F10 tumor cells into the left flank and assigned to experimental groups. At treatment initiation, animals were marked and each cage was labeled with the cage number, study number and the number of animals per cage.

Adjustment for in vivo administration with an application volume of 5 ml/kg was achieved by dilution of the stock solution in DPBS without Ca2+, Mg2+, pH 7.4 (Biochrom). And agents were dosed i.p. at 10 mg/kg q3dx6, starting treatment with tumor inoculation. Results are shown in FIGS. 1 and 2 and Tables 3-6.

TABLE 3

Mean tumor size per group as measured on 7 different time points after tumor inoculation

| days post inoculation | Mean tumor size [mm3] | |
|---|---|---|
| | Isotype ctrl | BAY 1905254 |
| 3 | 30.9 | 34.5 |
| 6 | 76.5 | 77.3 |
| 8 | 128.3 | 90.1 |
| 11 | 424.2 | 286.8 |
| 13 | 508.6 | 389.2 |
| 15 | 1442.6 | 1059.9 |
| 17 | 1919 | 1204 |

TABLE 4

Therapeutic efficacy shown as tumor size of the treatment group vs. isotype control (T/C)

| Isotype control | BAY1905254 |
|---|---|
| 1 | 0.63 |

TABLE 5

Mean tumor size per group as measured on 7 different time points after tumor inoculation

| days post inoculation | Mean tumor size [mm3] | |
|---|---|---|
| | Isotype ctrl | E10 |
| 3 | 31.35 | 19.77 |
| 6 | 75.06 | 80.56 |
| 8 | 100.37 | 75.56 |
| 11 | 271.1 | 257.17 |
| 13 | 402.52 | 399.08 |
| 15 | 984.44 | 1104.49 |
| 17 | 1193.58 | 1285.12 |

TABLE 6

Therapeutic efficacy shown as tumor size of the treatment group vs. isotype control (T/C)

| Isotype control | E10 |
|---|---|
| 1 | 1.08 |

7.2. B16-F10 Therapeutic Treatment, Synergistic Efficacy in Combination with aPD-L1

Eight weeks old female C57B1/6N Cr1 BR mice (body weight 18-20 g) from Charles River Deutschland, Sulzfeld were used for the B16-F10 tumor model. The experiment was initiated after an acclimatization period of 5 days. Animals were kept in a 12-hour light/dark cycle. Food and water was available ad libitum. Housing temperature was maintained at 21° C. Mice (n=11 per group) were s.c. inoculated with $1 \times 10^4$ B16F10 tumor cells into the left flank and assigned to experimental groups by stratified randomization (method for partitioning of the mice to groups with equal distribution of tumor size) on day 3 after tumor inoculation. At treatment initiation, animals were marked and each cage was labeled with the cage number, study number and the number of animals per cage.

Adjustment for in vivo administration with an application volume of 5 ml/kg was achieved by dilution of the stock solution in DPBS without Ca2+, Mg2+, pH 7.4 (Biochrom), and agents were dosed i.p. at 10 mg/kg q3dx5, starting d3. Results are shown in FIG. 3 and Tables 7-8.

TABLE 7

Mean tumor size per group as measured on 5 different time points after tumor inoculation

| days post inoculation | Isotype ctrl | aPDL1 | BAY-1905254 | BAY-1905254 + aPDL1 |
|---|---|---|---|---|
| 6 | 73.76 | 77.62 | 76.07 | 84.52 |
| 8 | 112.74 | 115.01 | 80.52 | 110.66 |
| 10 | 173.04 | 184.65 | 158.01 | 155.21 |
| 13 | 528.64 | 508.67 | 479.92 | 385.79 |
| 15 | 914.49 | 841.29 | 986.99 | 591.99 |

TABLE 8

Therapeutic efficacy shown as tumor size of the treatment group vs. isotype control (T/C)

| Isotype control | aPD-L1 | BAY1905254 | BAY1905254 + aPD-L1 |
|---|---|---|---|
| 1 | 0.92 | 1.08 | 0.65 |

7.3. CT26 therapeutic, synergistic efficacy with aPD-L1

Eight weeks old female Balb/cAnN mice (body weight 18-20 g) from Charles River Deutschland, Sulzfeld were used for the CT26 tumor model. The experiment was initiated after an acclimatization period of 6 days. Animals were kept in a 12-hour light/dark cycle. Food and water was available ad libitum. Housing temperature was maintained at 21° C. Mice (n=12 per group) were s.c. inoculated with $5 \times 10^5$ CT26 tumor cells into the left flank and assigned to experimental groups by stratified randomization (method for partitioning of the mice to groups with equal distribution of tumor size) on day 7 after tumor inoculation. At treatment initiation, animals were marked and each cage was labeled with the cage number, study number and the number of animals per cage.

Adjustment for in vivo administration with an application volume of 5 ml/kg was achieved by dilution of the stock solution in DPBS without Ca2+, Mg2+, pH 7.4 (Biochrom). aPD-L1 was dosed i.p. at 10 mg/kg q3dx3 and BAY1905254 was dosed i.p. at 3 mg/kg q3dx3, all treatments starting d7. Results are shown in FIG. 4 and Tables 9-10.

TABLE 9

Mean tumor size per group as measured on 4 different time points after tumor inoculation

| days post inoculation | Isotype ctrl | aPDL1 | BAY-1905254 | BAY-1905254 + aPDL1 |
|---|---|---|---|---|
| 7 | 133.95 | 131.65 | 136.38 | 141.18 |
| 10 | 215.71 | 170.73 | 227.41 | 160.19 |
| 13 | 411.77 | 232.03 | 367.22 | 195.8 |
| 15 | 605.73 | 384.88 | 576.28 | 228.04 |

TABLE 10

Therapeutic efficacy shown as tumor size of the treatment group vs. isotype control (T/C)

| Isotype control | aPD-L1 | BAY1905254 | BAY1905254 + aPD-L1 |
|---|---|---|---|
| 1 | 0.64 | 0.95 | 0.38 |

7.4. 3C9-D11-H11 therapeutic, synergistic efficacy with aPD-L1

Eight weeks old female Balb/cAnN mice (body weight 18-20 g) from Charles River Deutschland, Sulzfeld were used for the 3C9-D11-H11 tumor model.

The experiment was initiated after an acclimatization period of 12 days. Animals were kept in a 12-hour light/dark cycle. Food and water was available ad libitum. Housing temperature was maintained at 21° C. Mice (n=12 per group) were s.c. inoculated with $1 \times 10^4$ 3C9-D11-H11 tumor cells into the left flank and assigned to experimental groups by stratified randomization (method for partitioning of the mice to groups with equal distribution of tumor size) on day 8 after tumor inoculation. At treatment initiation, animals were marked and each cage was labeled with the cage number, study number and the number of animals per cage.

Adjustment for in vivo administration with an application volume of 5 ml/kg was achieved by dilution of the stock solution in DPBS without Ca2+, Mg2+, pH 7.4 (Biochrom). And agents were dosed i.p. at 10 mg/kg q3dx5, starting d8. Results are shown in FIG. 5 and Tables 11-12.

TABLE 11

Mean tumor size per group as measured on 6 different time points after tumor inoculation

| days post inoculation | Isotype ctrl | aPDL1 | BAY-1905254 | BAY-1905254 + aPDL1 |
|---|---|---|---|---|
| 7 | 64.64 | 64.74 | 63.28 | 63.97 |
| 10 | 95.23 | 94.85 | 67.18 | 64.44 |
| 14 | 273.61 | 177.51 | 198.87 | 68.16 |
| 16 | 441.36 | 216.11 | 314.06 | 66.94 |
| 18 | 748.65 | 290.22 | 574.54 | 74.08 |
| 21 | 1590.5 | 625.9 | 1377.9 | 106.6 |

TABLE 12

Therapeutic efficacy shown as tumor size of the
treatment group vs. isotype control (T/C)

| Isotype control | aPD-L1 | BAY1905254 | BAY1905254 + aPD-L1 |
|---|---|---|---|
| 1 | 0.39 | 0.87 | 0.07 |

8. Additional Combinations 8.1. Combination with Immunostimulatory CpG Oligos (an OVA Vaccine)

Nine weeks old female C57B1/6N Cr1 BR mice (body weight 18-20 g) from Charles River Deutschland, Sulzfeld were used for the B16F10 OVA tumor model. The model is a derivative of the B16-F10 cell line expressing the chicken allo-antigen ovalbumin which can be recognized by antigen-specific T cells. The experiment was initiated after an acclimatization period of 13 days. Animals were kept in a 12-hour light/dark cycle. Food and water was available ad libitum. Housing temperature was maintained at 21° C. Mice (n=12 per group) were s.c. inoculated with $1\times10^4$ B16-F10 OVA tumor cells into the left flank and assigned to experimental groups. At treatment initiation, animals were marked and each cage was labeled with the cage number, study number and the number of animals per cage.

Adjustment for in vivo administration of isotype control and BAY 1905254 with an application volume of 5 ml/kg was achieved by dilution of the stock solution in DPBS without Ca2+, Mg2+, pH 7.4 (Biochrom). Agents were dosed i.p. at 10 mg/kg q3dx3, starting day 8. 50 μg OVA (in 50 μl)+10 μg CPG (in 10 μl)+140 μl PBS=200 μl/mouse was applied subcutaneously to the left flank adjacent to the tumor, on day 9. The CpG oligonucleotide was ODN 1826 (5'-tccatgacgttcctgacgtt-3'; bases are phosphorothioate/nuclease resistant) that is specific for mouse TLR9 was used (Invivogen MA-1826-5). Results are shown in FIG. 6 and Tables 13-14.

TABLE 13

Mean tumor size per group as measured on 6
different time points after tumor inoculation

| days post inoculation | Mean tumor size [mm3] | | | |
|---|---|---|---|---|
| | Control | BAY 1905254 | OVA + CpG | BAY 1905254 + OVA + CpG |
| 9 | 57.9 | 66.09 | 63.69 | 68.02 |
| 11 | 123.7 | 137.52 | 151.49 | 112.2 |
| 14 | 357.38 | 314.75 | 257.91 | 177.8 |
| 16 | 617.65 | 483.38 | 353.64 | 236.92 |
| 18 | 1076.80 | 711.93 | 538.62 | 406.97 |

TABLE 14

Therapeutic efficacy shown as tumor size of
the treatment group vs. Control (T/C)

| Control | BAY1905254 | OVA + CpG | BAY1905254 + OVA + CpG |
|---|---|---|---|
| 1 | 0.66 | 0.5 | 0.38 |

8.2. Combination with Docetaxel

Eight weeks old female C57B1/6N Cr1 BR mice (body weight 18-20 g) from Charles River Deutschland, Sulzfeld were used for the B16-F10 OVA tumor model. The model is a derivative of the B16F10 cell line expressing the allo-antigen ovalbumin which can be recognized by antigen-specific T cells. The experiment was initiated after an acclimatization period of 5 days. Animals were kept in a 12-hour light/dark cycle. Food and water was available ad libitum. Housing temperature was maintained at 21° C. Mice (n=12 per group) were s.c. inoculated with $1\times10^4$ B16F10 OVA tumor cells into the left flank and assigned to experimental groups. At treatment initiation, animals were marked and each cage was labeled with the cage number, study number and the number of animals per cage.

Adjustment for in vivo administration of isotype control and BAY 1905254 with an application volume of 5 ml/kg was achieved by dilution of the stock solution in DPBS without Ca2+, Mg2+, pH 7.4 (Biochrom). Agents were dosed i.p. at 10 mg/kg q3dx3, starting day 8. Docetaxel was dose once at 20 mg/kg, i.v. on day 8, stock solution of 80 mg/4ml diluted with 0,9% NaCl for infusion purposes. Results are shown in FIG. 7 and Tables 15-16.

TABLE 15

Mean tumor size per group as measured on 4 different
time points after tumor inoculation

| days post inoculation | Mean tumor size [mm3] | | | |
|---|---|---|---|---|
| | Control | Docetaxel | BAY 1905254 | BAY 1905254 + Docetaxel |
| 8 | 85.87 | 86.56 | 86.26 | 80.90 |
| 11 | 128.11 | 100.78 | 97.06 | 81.91 |
| 14 | 287.01 | 165.78 | 207.75 | 109.83 |
| 16 | 451.99 | 305.33 | 382.66 | 177.66 |

TABLE 16

Therapeutic efficacy shown as tumor size of
the treatment group vs. Control (T/C)

| Control | Docetaxel | BAY-1905254 | BAY 1905254 + Docetaxel |
|---|---|---|---|
| 1 | 0.74 | 0.86 | 0.54 |

8.3. Combination with C4.4A ADC

Nine weeks old female Balb/cAnN mice (body weight 18-20 g) from Charles River Deutschland, Sulzfeld were used for the CT26 C4.4a tumor model. This model is a derivative of the parental CT26 model expressing murine C4.4a on the surface of the tumor cells.

The experiment was initiated after an acclimatization period of 15 days. Animals were kept in a 12-hour light/dark cycle. Food and water was available ad libitum. Housing temperature was maintained at 21° C. Mice (n=12 per group) were s.c. inoculated with $1\times10^5$ CT26 tumor cells into the left flank and assigned to experimental groups by stratified randomization (method for partitioning of the mice to groups with equal distribution of tumor size) on day 6 after tumor inoculation.

At treatment initiation, animals were marked and each cage was labeled with the cage number, study number and the number of animals per cage. Adjustment for in vivo administration with an application volume of 10 ml/kg were prepared by dilution of the stock solution in DPBS without Ca2+, Mg2+, pH 7.4 (Biochrom). Agents (Control+BAY 1905254) were dosed i.p. at 10 mg/kg q3dx5, starting day 6.

C4.4A ADC (antibody-drug conjugate BAY1129980), which is composed of an antibody against a structural homolog of the urokinase-type plasminogen activator receptor (uPAR) and tumor-associated antigen, C4.4a, and conjugated with a cytotoxic agent, was dosed 10 mg/kg i.v. q4d×3, starting day 6. Results are shown in FIG. 8 and Tables 17-18.

TABLE 17

Mean tumor size per group as measured on 6 different time points after tumor inoculation

| days post inoculation | Control | C4.4A ADC | BAY 1905254 | BAY 1905254 + C4.4A ADC |
|---|---|---|---|---|
| 6 | 55.72 | 50.79 | 56.89 | 55.31 |
| 10 | 151.53 | 115.08 | 141.28 | 126.25 |
| 12 | 227.70 | 145.91 | 220.99 | 134.02 |
| 14 | 273.92 | 194.20 | 260.95 | 93.15 |
| 17 | 417.31 | 425.73 | 566.58 | 182.83 |
| 19 | 627.05 | 633.25 | 706.01 | 334.84 |

TABLE 18

Therapeutic efficacy shown as tumor size of the treatment group vs. Control (T/C)

| Control | C4.4A ADC | BAY-1905254 | BAY1905254 + C4.4A ADC |
|---|---|---|---|
| 1 | 1.01 | 1.13 | 0.53 |

SEQUENCES

The sequences shown in the following table are referred to herein. In case there is an ambiguity between this table and the WIPO standard sequence listing that forms part of the present specification and its disclosure, the sequences and qualifiers in this table shall be deemed the correct ones.

| | | |
|---|---|---|
| 1 | 59-08.B02 BAY1905254 HCDR1 | SYAIS |
| 2 | 59-08.B02 BAY1905254 HCDR2 | GIIPILGIANYAQKFQG |
| 3 | 59-08.B02 BAY1905254 HCDR3 | ARGRLPYGDFWDS |
| 4 | 59-08.B02 BAY1905254 LCDR1 | RSSQSLLYSNGYNYLD |
| 5 | 59-08.B02 BAY1905254 LCDR2 | LGSNRAS |
| 6 | 59-08.B02 BAY1905254 LCDR3 | MQALQTPLT |
| 7 | 59-08.B02 heavy chain VD\| BAY1905254 | QVQLVQSGAEVKKPGSSVKVSCKASGGTFSSYAISWVRQAPGQGLEWMGGII PILGIANYAQKFQGRVTITADKSTSTAYMELSSLRSEDTAVYYCARGRLPYGDF WDSWGQGTLVTVSS |
| 8 | 59-08.B02-light chain VD\| BAY1905254 | DIVMTQSPLSLPVTPGEPASISCRSSQSLLYSNGYNYLDWYLQKPGQSPQLLIYL GSNRASGVPDRFSGSGSGTDFTLKISRVEAEDVGVYYCMQALQTPLTFGGGTK LEIR |
| 9 | 61-02.C05 heavy chain VD | EVQLVESGGGVVQPGGSLRLSCAASGFTFSSYAMSWVRQAPGKGLEWVSGIS SSGGSTQYADSVKGRFTVSRDNSKNTLYLQMKSLRAEDTALYYCAKDFVGVLP DAFDIWGQGTMVTVSS |
| 10 | 61-02.C05 light chain VD | DIQLTQSPSSLSASVGDRVTITCQASQDTNKYLNWYQQKPGKAPELLIYGASTL ESGVPPRFSASGSGTDFTLTINSLQPEDIGRYYCQQYHIPPPSFGGGTKLEIK |
| 11 | 56-02.E08 heavy chain VD | EVQLVQSGAEVKKPGESLKISCKASGYSFTTYWIGWVRQVPGKGLEWMGIIYP GDYDTRYSPSFQGQVTISADKSINTAYLQWSSLEASDSAMYYCAIGEPFDYWG QGTLVTVSS |
| 12 | 56-02.E08 light chain VD | DVVMTQSPLSLPVTPGEPASISCRSSQSLLHANGYNYLDWYLQKPGQSPQLLIY LGSNRASGVPDRFSGSGSGTDFTLKISRVETEDVGVYYCMQALQTPLTFGGGT KVEIK |
| 13 | 74.15.G09 heavy chain VD | EVQLVESGGGVVQPGRSLRLSCAASGFTFSSYGMHWVRQAPGKGLEWVAVI SYDGSNKYYADSVKGRFTISRDNSKNTLYLQMNSLRAEDTAVYYCAKESPSVG LGSYYDFWSGLYGMDVWGQGTTVTVSS |

| | | |
|---|---|---|
| 14 | 74.15.G09 light chain VD | EIVLTQSPGTLSLSPGERVTLSCRTGQRVENLFIAWYQQKPGQAPRLLLYGASN RATGIPDRFSGSGSGTDFTLTISRLEPEDSAVYYCQQYDDSGITFGQGTRLEIK |
| 15 | 56.02.E10 heavy chain VD | QVQLVESGGGLVKPGGSLRLSCAASGFTFSNYGMHWVRQAPGKGPEWLAFI RYDGSKKYYADSVRGRFTISRDNSKNMLYLQMNSLRTEDTAVYYCAKEGIAAP GSGYYYGMDVWGQGTTVTVSS |
| 16 | 56.02.E10 light chain VD | QSALTQPASVSGSPGQSITISCSGTTTDVGRYTLVSWYQHHPGKAPKLIIFEVN KRPSGVSSRFSGSKSGNTASLTISGLQTEDEADYFCCSYTGTTVIFGGGTQLTVL |
| 17 | CPG Oligonucleotide ODN 1826 | tccatgacgttcctgacgtt |
| 18 | 61-02.C05 HCDR1 | SYAMS |
| 19 | 61-02.C05 HCDR2 | GISSSGGSTQYADSVKG |
| 20 | 61-02.C05 HCDR3 | DFVGVLPDAFDI |
| 21 | 61-02.C05 LCDR1 | QASQDTNKYLN |
| 22 | 61-02.C05 LCDR2 | GASTLES |
| 23 | 61-02.C05 LCDR3 | QQYHIPPPS |
| 24 | 56-02.E08 HCDR1 | TYWIG |
| 25 | 56-02.E08 HCDR2 | IIYPGDYDTRYSPSFOG |
| 26 | 56-02.E08 HCDR3 | AIGEPFDY |
| 27 | 56-02.E08 LCDR1 | RSSQSLLHANGYNYLD |
| 28 | 56-02.E08 LCDR2 | LGSNRAS |
| 29 | 56-02.E08 LCDR3 | MQALQTPLT |
| 30 | 74.15.G09 HCDR1 | SYGMH |
| 31 | 74.15.G09 HCDR2 | VISYDGSNKYYADSVKG |
| 32 | 74.15.G09 HCDR3 | AKESPSVGLGSYYDFWSGLYGMDV |
| 33 | 74.15.G09 LCDR1 | RTGQRVENLFIA |
| 34 | 74.15.G09 LCDR2 | GASNRAT |
| 35 | 74.15.G09 LCDR3 | QQYDDSGIT |
| 36 | 56.02.E10 HCDR1 | NYGMH |
| 37 | 56.02.E10 HCDR2 | FIRYDGSKKYYADSVRG |
| 38 | 56.02.E10 HCDR3 | EGIAAPGSGYYYGMDV |
| 39 | 56.02.E10 LCDR1 | SGTTTDVGRYTLVS |
| 40 | 56.02.E10 LCDR2 | EVNKRPS |
| 41 | 56.02.E10 LCDR3 | CSYTGTTVI |
| 42 | 59-08.B02 heavy chain BAY1905254 | QVQLVQSGAEVKKPGSSVKVSCKASGGTFSSYAISWVRQAPGQGLEWMGGII PILGIANYAQKFQGRVTITADKSTSTAYMELSSLRSEDTAVYYCARGRLPYGDF WDSWGQGTLVTVSSASTKGPSVFPLAPCSRSTSESTAALGCLVKDYFPEPVTV SWNSGALTSGVHTFPAVLQSSGLYSLSSVVTVPSSNFGTQTYTCNVDHKPSNT KVDKTVERKCCVECPPCPAPPVAGPSVFLFPPKPKDTLMISRTPEVTCVVVDVS HEDPEVQFNWYVDGVEVHNAKTKPREEQFNSTFRVVSVLTVVHQDWLNGK EYKCKVSNKGLPAPIEKTISKTKGQPREPQVYTLPPSREEMTKNQVSLTCLVKGF YPSDIAVEWESNGQPENNYKTTPPMLDSDGSFFLYSKLTVDKSRWQQGNVFS CSVMHEALHNHYTQKSLSLSPG |
| 43 | 59-08.B02-light chain BAY1905254 | DIVMTQSPLSLPVTPGEPASISCRSSQSLLYSNGYNYLDWYLQKPGQSPQLLIYL GSNRASGVPDRFSGSGSGTDFTLKISRVEAEDVGVYYCMQALQTPLTFGGGTK LEIRRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSENR GEC |

| 44 | 61-02.C05 heavy chain | EVQLVESGGGVVQPGGSLRLSCAASGFTFSSYAMSWVRQAPGKGLEWVSGIS SSGGSTQYADSVKGRFTVSRDNSKNTLYLQMKSLRAEDTALYYCAKDFVGVLP DAFDIWGQGTMVTVSSASTKGPSVFPLAPCSRSTSESTAALGCLVKDYFPEPV TVSWNSGALTSGVHTFPAVLQSSGLYSLSSVVTVPSSNFGTQTYTCNVDHKPS NTKVDKTVERKCCVECPPCPAPPVAGPSVFLFPPKPKDTLMISRTPEVTCVVVD VSHEDPEVQFNWYVDGVEVHNAKTKPREEQFNSTFRVVSVLTVVHQDWLN GKEYKCKVSNKGLPAPIEKTISKTKGQPREPQVYTLPPSREEMTKNQVSLTCLV KGFYPSDIAVEWESNGQPENNYKTTPPMLDSDGSFFLYSKLTVDKSRWQQG NVFSCSVMHEALHNHYTQKSLSLSPG |
| 45 | 61-02.C05 light chain | DIQLTQSPSSLSASVGDRVTITCQASQDTNKYLNWYQQKPGKAPELLIYGASTL ESGVPPRFSASGSGTDFTLTINSLQPEDIGRYYCQQYHIPPPSFGGGTKLEIKRT VAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSFNRGEC |
| 46 | 56-02.E08 heavy chain | EVQLVQSGAEVKKPGESLKISCKASGYSFTTYWIGWVRQVPGKGLEWMGIIYP GDYDTRYSPSFQGQVTISADKSINTAYLQWSSLEASDSAMYYCAIGEPFDYWG QGTLVTVSSASTKGPSVFPLAPCSRSTSESTAALGCLVKDYFPEPVTVSWNSGA LTSGVHTFPAVLQSSGLYSLSSVVTVPSSNFGTQTYTCNVDHKPSNTKVDKTVE RKCCVECPPCPAPPVAGPSVFLFPPKPKDTLMISRTPEVTCVVVDVSHEDPEV QFNWYVDGVEVHNAKTKPREEQFNSTFRVVSVLTVVHQDWLNGKEYKCKVS NKGLPAPIEKTISKTKGQPREPQVYTLPPSREEMTKNQVSLTCLVKGFYPSDIAV EWESNGQPENNYKTTPPMLDSDGSFFLYSKLTVDKSRWQQGNVFSCSVMHE ALHNHYTQKSLSLSPG |
| 47 | 56-02.E08 light chain | DVVMTQSPLSLPVTPGEPASISCRSSQSLLHANGYNYLDWYLQKPGQSPQLLIY LGSNRASGVPDRFSGSGSGTDFTLKISRVETEDVGVYYCMQALQTPLTFGGGT KVEIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKSFN RGEC |
| 48 | 74.15.G09 heavy chain | EVQLVESGGGVVQPGRSLRLSCAASGFTFSSYGMHWVRQAPGKGLEWVAVI SYDGSNKYYADSVKGRFTISRDNSKNTLYLQMNSLRAEDTAVYYCAKESPSVG LGSYYDFWSGLYGMDVWGQGTTVTVSSASTKGPSVFPLAPCSRSTSESTAAL GCLVKDYFPEPVTVSWNSGALTSGVHTFPAVLQSSGLYSLSSVVTVPSSNFGT QTYTCNVDHKPSNTKVDKTVERKCCVECPPCPAPPVAGPSVFLFPPKPKDTLM ISRTPEVTCVVVDVSHEDPEVQFNWYVDGVEVHNAKTKPREEQFNSTFRVVS VLTVVHQDWLNGKEYKCKVSNKGLPAPIEKTISKTKGQPREPQVYTLPPSREE MTKNQVSLTCLVKGFYPSDIAVEWESNGQPENNYKTTPPMLDSDGSFFLYSKL TVDKSRWQQGNVFSCSVMHEALHNHYTQKSLSLSPG |
| 49 | 74.15.G09 light chain | EIVLTQSPGTLSLSPGERVTLSCRTGQRVENLFIAWYQQKPGQAPRLLLYGASN RATGIPDRFSGSGSGTDFTLTISRLEPEDSAVYYCQQYDDSGITFGQGTRLEIKR TVAAPSVFIFPPSDEQLKSGTASVVCLLNNFYPREAKVQWKVDNALQSGNSQE SVTEQDSKDSTYSLSSTLTLSKADYEKHKVYACEVTHQGLSSPVTKSFNRGEC |
| 50 | 56.02.E10 heavy chain | QVQLVESGGGLVKPGGSLRLSCAASGFTFSNYGMHWVRQAPGKGPEWLAFI RYDGSKKYYADSVRGRFTISRDNSKNMLYLQMNSLRTEDTAVYYCAKEGIAAP GSGYYYGMDVWGQGTTVTVSSASTKGPSVFPLAPCSRSTSESTAALGCLVKDY FPEPVTVSWNSGALTSGVHTFPAVLQSSGLYSLSSVVTVPSSNFGTQTYTCNV DHKPSNTKVDKTVERKCCVECPPCPAPPVAGPSVFLFPPKPKDTLMISRTPEVT CVVVDVSHEDPEVQFNWYVDGVEVHNAKTKPREEQFNSTFRVVSVLTVVHQ DWLNGKEYKCKVSNKGLPAPIEKTISKTKGQPREPQVYTLPPSREEMTKNQVS LTCLVKGFYPSDIAVEWESNGQPENNYKTTPPMLDSDGSFFLYSKLTVDKSRW QQGNVFSCSVMHEALHNHYTQKSLSLSPG |
| 51 | 56.02.E10 light chain | QSALTQPASVSGSPGQSITISCSGTTTDVGRYTLVSWYQHHPGKAPKLIIFEVN KRPSGVSSRFSGSKSGNTASLTISGLQTEDEADYFCCSYTGTTVIFGGGTQLTVL GQPKAAPSVTLFPPSSEELQANKATLVCLISDFYPGAVTVAWKADSSPVKAGV ETTTPSKQSNNKYAASSYLSLTPEQWKSHRSYSCQVTHEGSTVEKTVAPTECS |

What is claimed is:

1. A pharmaceutical combination comprising an ILDR2 antagonist plus optionally one or more other therapeutically active compounds,
   wherein the ILDR2 antagonist is an anti-ILDR2 antibody, or a fragment or derivative thereof, or a modified antibody format, having ILDR2 binding properties which comprises at least the following CDR heavy chain (HC) sequences and paired CDR light chain (LC) sequences:
   SEQ ID NO:1 CDR1 HC,
   SEQ ID NO:2 CDR2 HC,
   SEQ ID NO:3 CDR3 HC,
   SEQ ID NO:4 CDR1 LC,
   SEQ ID NO:5 CDR2 LC, and
   SEQ ID NO:6 CDR3 LC.

2. The combination according to claim 1, wherein at least one of the one or more other therapeutically active compounds is selected from the group consisting of:
   a PD-L1 antagonist,
   a taxane or taxane derivative,
   a vaccine, a CpG oligodeoxynucleotide, and
a compound targeting c4.4A.

3. The combination according to claim 1, wherein the ILDR2 antagonist and the one or more other therapeutically active compounds are
provided in the same dosage unit, or
provided in individual dosage units.

4. The combination according to claim 1, wherein the ILDR2 antagonist and the one or more other therapeutically active compounds are configured to be
administered simultaneously, or
administered sequentially.

5. The combination according to claim 1, wherein the ILDR2 antagonist is an antibody mimetic.

6. A method for treating a patient
suffering from,
and/or
diagnosed with
a neoplastic disease, cancer, or an immune disease or disorder, the method comprising administering to said patient an ILDR2 antagonist or antibody, or fragment or derivative or modified antibody format, or a combination comprising an ILDR2 antagonist, according to claim 1, in one or more therapeutically efficient dosages.

7. An anti-ILDR2 antibody, or a fragment or derivative thereof, or a modified antibody format, having ILDR2 binding properties, which comprises at least the following CDR heavy chain (HC) sequences and paired CDR light chain (LC) sequences:
SEQ ID NO:1 CDR1 HC,
SEQ ID NO:2 CDR2 HC,
SEQ ID NO:3 CDR3 HC,
SEQ ID NO:4 CDR1 LC,
SEQ ID NO:5 CDR2 LC, and
SEQ ID NO:6 CDR3 LC.

8. The anti-ILDR2 antibody, or fragment or derivative thereof, or modified antibody format, according to claim 7, which comprises at least one heavy chain (HC) and at least one light chain (LC) variable region (VD) sequence that are 95% identical to the following sequences:
SEQ ID NO:7 HC VD, and
SEQ ID NO:8 LC VD.

9. The anti-ILDR2 antibody, or fragment or derivative thereof, or modified antibody format, according to claim 7, which comprises at least one heavy chain (HC) and at least one light chain (LC) sequence that are 95% identical to the following sequences:
SEQ ID NO:42 HC, and
SEQ ID NO:43 LC.

10. The ILDR2 antibody, or fragment or derivative thereof, or modified antibody format, according to claim 7, which dissociates from human ILDR2 with a $K_d$ of 25 nM ($2,5 \times 10^{-8}$M) or less, determined by fluorescence-activated cell scanning (FACS).

11. An antibody-drug conjugate, comprising an ILDR2 antibody or a fragment or derivative thereof, or a modified antibody format, according to claim 7.

12. An isolated nucleic acid sequence or a set thereof, that encodes an ILDR2 antibody, or fragment or derivative thereof, or a modified antibody format, according to claim 7.

13. A vector comprising at least one nucleic acid sequence according to claim 12.

14. An isolated cell expressing an ILDR2 antibody, or fragment or derivative thereof, or a modified antibody format, according to claim 7.

15. An anti-ILDR2 antibody, or a fragment or derivative thereof, or a modified antibody format, having ILDR2 binding properties, which comprises at least one combination of three CDR heavy chain sequences and paired CDR light chain (LC) sequences selected from the group consisting of:
SEQ ID NOs: 18-20, as HC CDR 1-3, respectively, paired with SEQ ID NOs:21-23 as LC CDR 1-3, respectively;
SEQ ID NOs:24-26 as HC CDR 1-3, respectively, together with SEQ ID NOs: 27-29 as LC CDR 1-3, respectively;
SEQ ID NOs:30-32 as HC CDR 1-3, respectively, together with SEQ ID NO: 33-35 as LC CDR 1-3, respectively; and
SEQ ID NOs:36-38 as HC CDR 1-3, respectively; together with SEQ ID NOs:39-41 as LC CDR 1-3, respectively.

16. An anti-ILDR2 antibody, or a fragment or derivative thereof, or a modified antibody format, having ILDR2 binding properties, which comprises at least one combination of a heavy chain (HC) and paired light chain (LC) variable region (VD) sequence selected from the group consisting of:
SEQ ID NO:9, as the HC VD, paired with SEQ ID NO:10 as the LC VD;
SEQ ID NO:11 as the HC VD, paired with SEQ ID NO:12 as the LC VD;
SEQ ID NO:13, as the HC VD, paired with SEQ ID NO:14 as the LC VD; and
SEQ ID NO:15, as the HC VD, paired with SEQ ID NO:16 as the LC VD.

17. An anti-ILDR2 antibody, or a fragment or derivative thereof, or a modified antibody format, having ILDR2 binding properties, which comprises at least one combination of a heavy chain (HC) and light chain (LC) sequence selected from the group consisting of:
SEQ ID NO:44, as the HC, paired with SEQ ID NO:45, as the LC;
SEQ ID NO:46, as the HC, paired with SEQ ID NO:47, as the LC;
SEQ ID NO:48, as the HC, paired with SEQ ID NO:49, as the LC; and
SEQ ID NO:50, as the HC, paired with SEQ ID NO:51, as the LC.

18. An anti-ILDR2 antibody selected from the group consisting of 61-02.C05, 56-02.E08, 74-15.G09, and 59-08.B02.

* * * * *